United States Patent
Morisaki

(10) Patent No.: US 9,872,726 B2
(45) Date of Patent: Jan. 23, 2018

(54) GRIPPING UNIT AND BIPOLAR TREATMENT INSTRUMENT

(71) Applicant: OLYMPUS CORPORATION, Hachioji-shi, Tokyo (JP)

(72) Inventor: Kazuhiro Morisaki, Yokohama (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/265,626

(22) Filed: Sep. 14, 2016

(65) Prior Publication Data

US 2017/0000556 A1    Jan. 5, 2017

Related U.S. Application Data

(63) Continuation of application No. PCT/JP2015/055633, filed on Feb. 26, 2015.

(30) Foreign Application Priority Data

Mar. 14, 2014    (JP) .................. 2014-051763

(51) Int. Cl.
*A61B 18/18*    (2006.01)
*A61B 18/14*    (2006.01)
(Continued)

(52) U.S. Cl.
CPC .. *A61B 18/1445* (2013.01); *A61B 17/320092* (2013.01); *A61B 18/1206* (2013.01);
(Continued)

(58) Field of Classification Search
CPC ........ A61B 17/320092; A61B 18/1206; A61B 18/1445; A61B 2018/00077;
(Continued)

(56) References Cited

U.S. PATENT DOCUMENTS

2006/0259054 A1\* 11/2006 Masuda ................. A61B 17/29
606/169
2007/0043297 A1\* 2/2007 Miyazawa ......... A61B 18/1445
600/471
(Continued)

FOREIGN PATENT DOCUMENTS

EP    2 158 867 A1    3/2010
EP    2 484 301 A1    8/2012
(Continued)

OTHER PUBLICATIONS

Oct. 4, 2016 International Preliminary Report on Patentability issued in International Application No. PCT/JP2015/055633.
(Continued)

*Primary Examiner* — Michael Peffley
*Assistant Examiner* — Amanda Zink
(74) *Attorney, Agent, or Firm* — Oliff PLC

(57) ABSTRACT

A gripping unit includes a supporting section in which at least its entire surface is made of an insulating material, and a swing section swingable about a swing axis relative to the supporting section. The swing section includes a jaw-side facing surface opposed to a treatment section, and a jaw-side electrode section functioning as an electrode when high-frequency energy is transmitted. The support member covers the swing section from a distal direction, both of width directions, and an open direction of the jaw, and the swing section is externally exposed only on the jaw-side facing surface.

16 Claims, 11 Drawing Sheets

(51) Int. Cl.
*A61B 17/32* (2006.01)
*A61B 18/12* (2006.01)
A61B 18/00 (2006.01)
A61B 17/28 (2006.01)

(52) U.S. Cl.
CPC ............... *A61B 2017/2825* (2013.01); *A61B 2018/00077* (2013.01); *A61B 2018/00083* (2013.01); *A61B 2018/00994* (2013.01); *A61B 2018/126* (2013.01)

(58) Field of Classification Search
CPC ........... A61B 2018/00083; A61B 2018/00994; A61B 2018/126
See application file for complete search history.

(56) References Cited

U.S. PATENT DOCUMENTS

2008/0132887 A1* 6/2008 Masuda ............. A61B 18/1445 606/37
2010/0057084 A1 3/2010 Hanna
2011/0278343 A1 11/2011 Knodel et al.
2012/0277778 A1 11/2012 Masuda et al.
2013/0303949 A1 11/2013 Kawaguchi et al.

FOREIGN PATENT DOCUMENTS

| JP | 2004-209042 A | 7/2004 |
| JP | 2009-160404 A | 7/2009 |
| JP | 2011-206265 A | 10/2011 |
| JP | 4976597 B2 | 7/2012 |

OTHER PUBLICATIONS

May 26, 2015 International Search Report issued in International Patent Application No. PCT/JP2015/055633.
Mar. 29, 2016 Office Action issued in Japanese Patent Application No. 2016-501688.
Oct. 16, 2017 Search Report issued in European Patent Application No. 15761280.5.

* cited by examiner

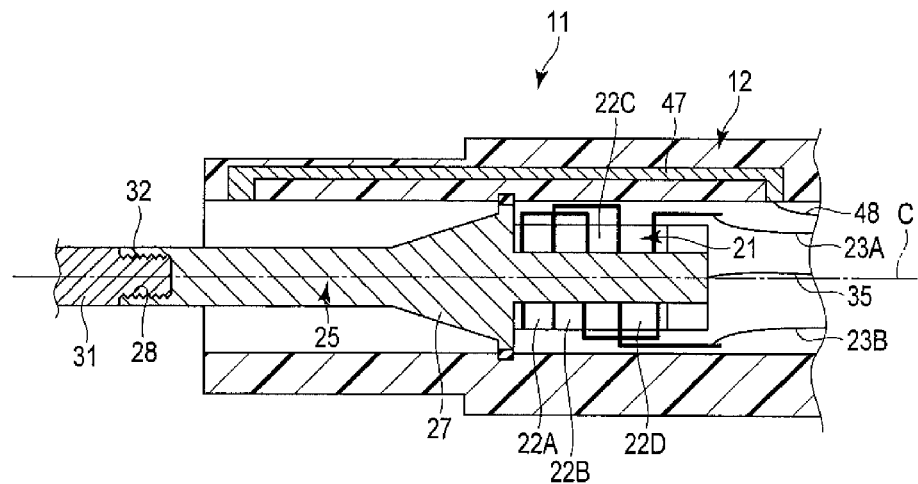
F I G. 2
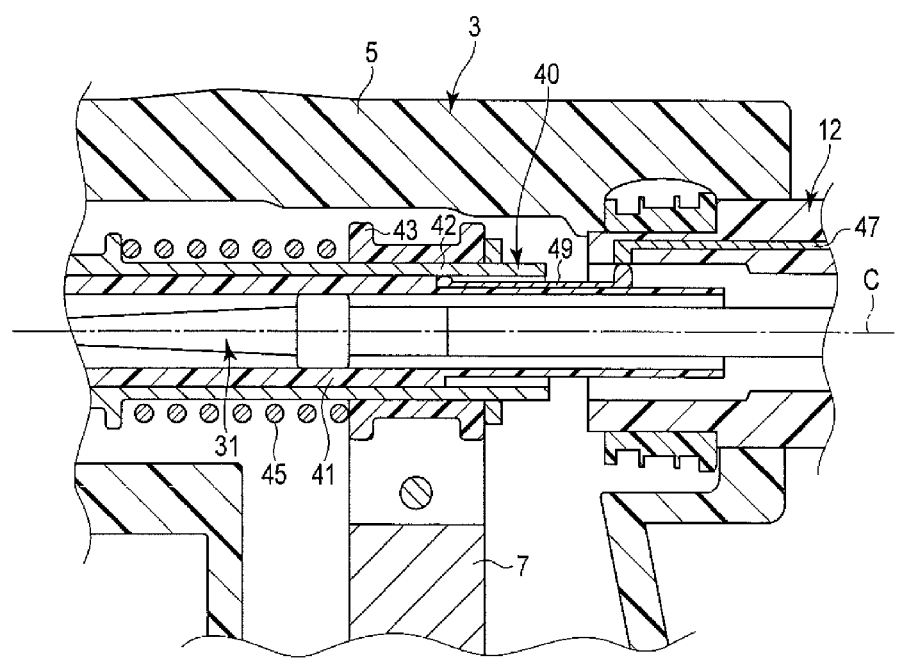
F I G. 3

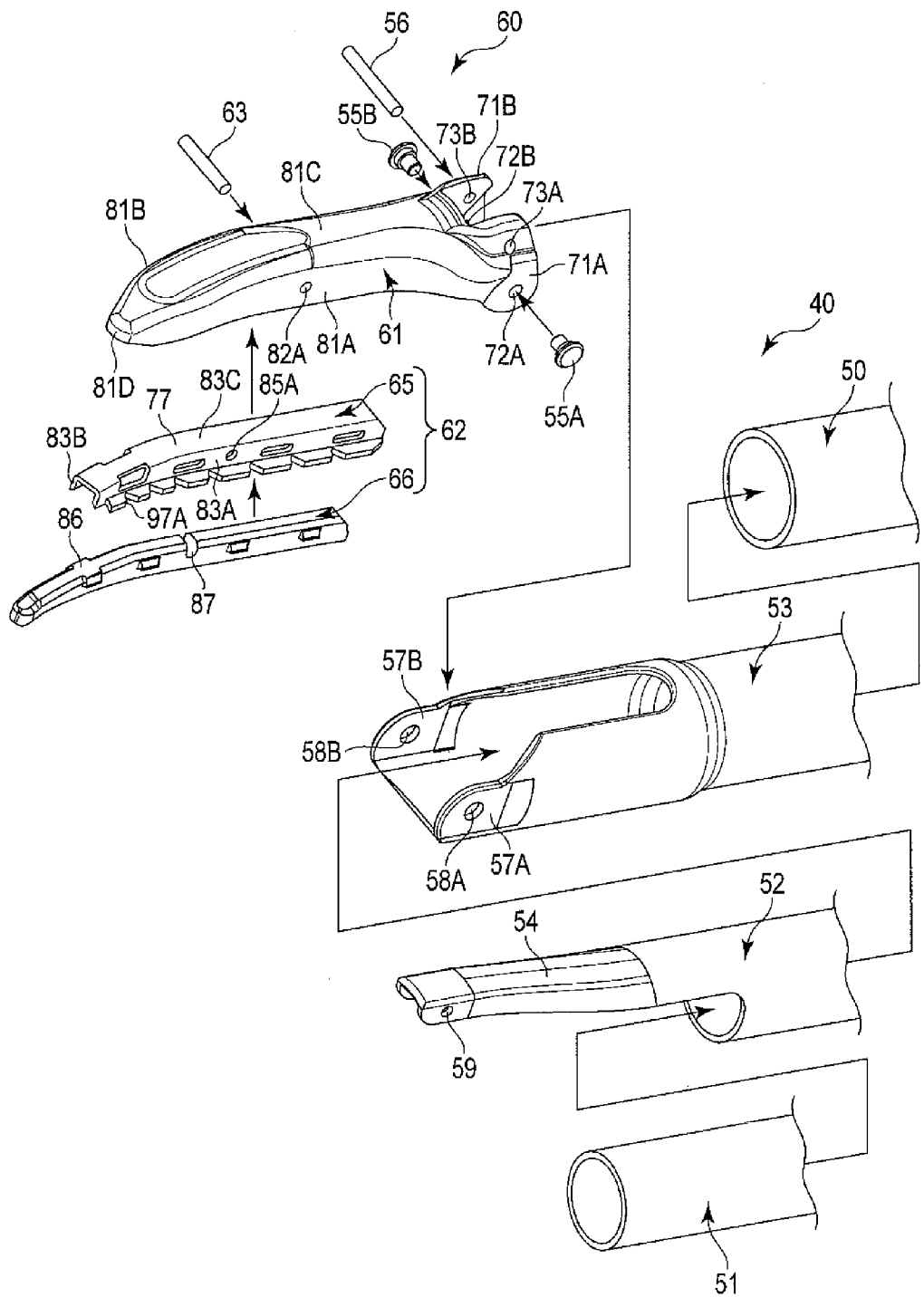
F I G. 6

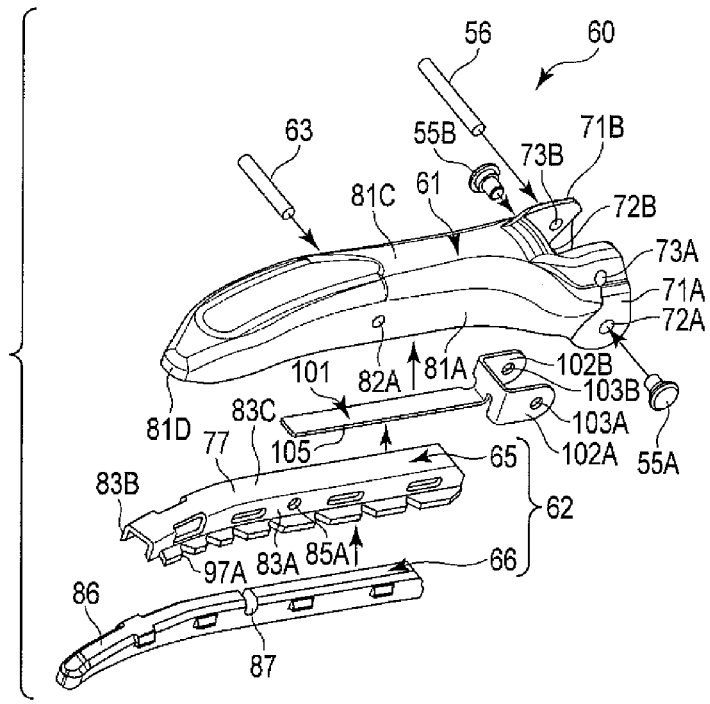
F I G. 11
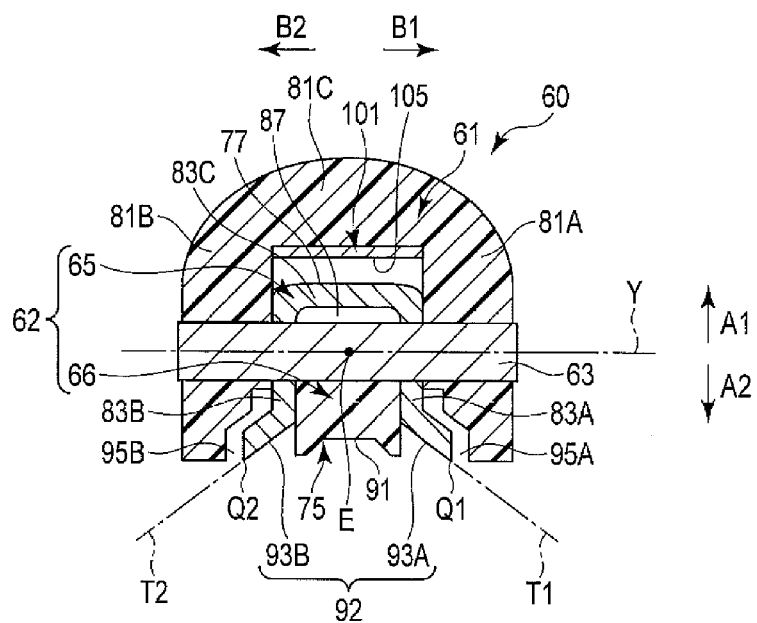
F I G. 12

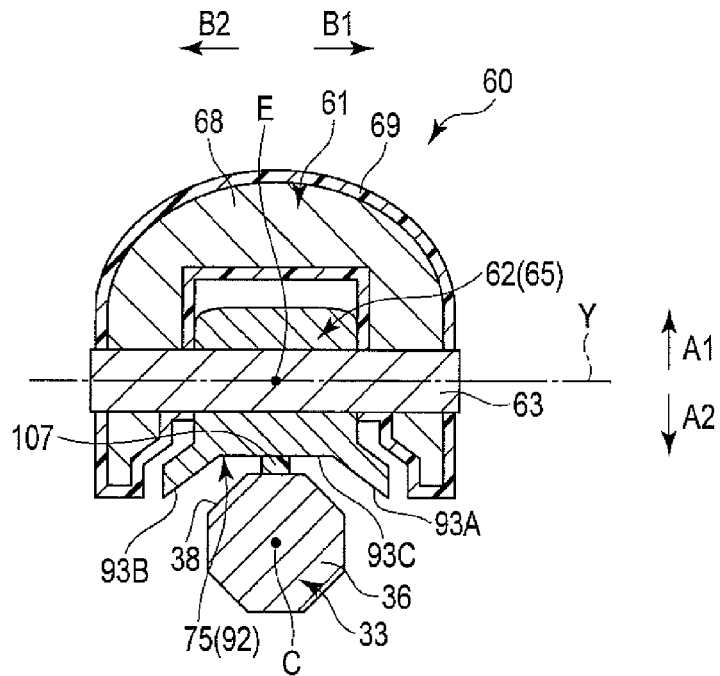
F I G. 15
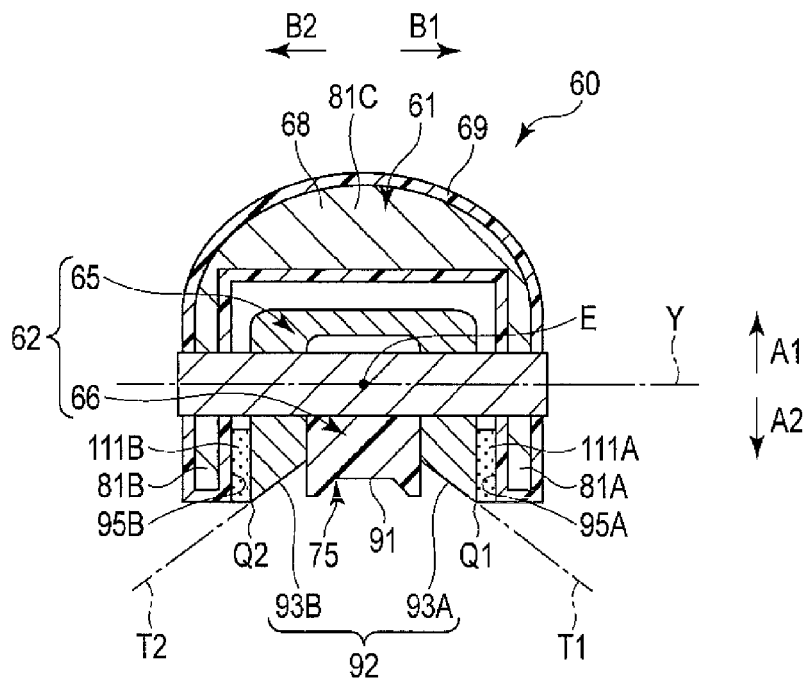
F I G. 16

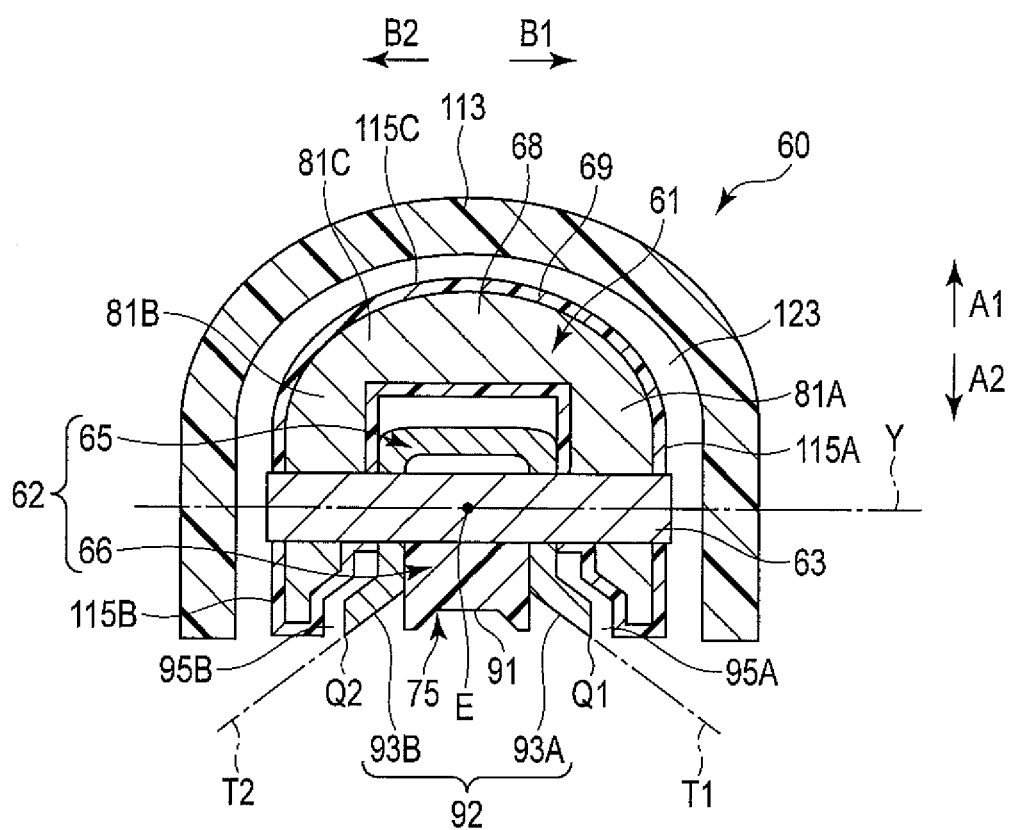
F I G. 19

GRIPPING UNIT AND BIPOLAR TREATMENT INSTRUMENT

CROSS-REFERENCE TO RELATED APPLICATIONS

This is a Continuation Application of PCT Application No. PCT/JP2015/055633, filed Feb. 26, 2015 and based upon and claiming the benefit of priority from prior Japanese Patent Application No. 2014-051763, filed Mar. 14, 2014, the entire contents of which are incorporated herein by reference.

BACKGROUND OF THE INVENTION

1. Field of the Invention

The present invention relates to a gripping unit which is openable and closable with respect to a treatment section of a probe, and a bipolar treatment instrument which performs treatment on a treated target gripped between the treatment section of the probe and the gripping unit.

2. Description of the Related Art

U.S. Patent Application Publication No. 2011/0278343 discloses a bipolar treatment instrument which includes a probe in which a treatment section is provided in its distal portion, and a jaw as a gripping unit which is openable and closable with respect to the treatment section and which performs treatment using a high-frequency current (high-frequency energy). The treatment section of such a bipolar treatment instrument functions as a probe-side electrode section (a first electrode section) when high-frequency energy is transmitted (supplied) through the probe. The jaw (the gripping unit) is provided with a supporting section and a swing section configured to swing with respect to the supporting section. The swing section is coupled to the supporting section with a spring serving as a coupling member being interposed therebetween in such a manner that the swing section is swingable about the swing axis parallel to a width direction of the jaw. The swing section functions as a jaw-side electrode section (a second electrode section) when high-frequency energy is transmitted (supplied) through a conductive portion provided in a sheath through which a probe is inserted and the support section of the jaw.

A jaw-side facing surface opposed to the treatment section is provided in the swing section, and when a treated target, such as living tissue, etc., is gripped between the treatment section of the probe and the jaw, the jaw is abutted to the treated target on the jaw-side facing surface of the swing section. Since the swing section in which the jaw-side facing surface abutted to the treated target is swingable about the swing axis, the force between the jaw and the treatment section to grasp the treated target in the case where the distal portion of the jaw-side facing surface (the distal portion of the jaw) is abutted to the treated target is approximately the same as the case where the proximal portion of the jaw-side facing surface (the proximal portion of the jaw) is abutted to the treated target. In other words, the gripping force between the jaw and the treatment section can be maintained nearly uniform, even when the position where the jaw-side facing surface is abutted to the treated target in a direction parallel to an extended axis of the jaw (a distal direction and a proximal direction) is changed.

BRIEF SUMMARY OF THE INVENTION

According to one aspect of the invention, a gripping unit which is extended along an extension axis from a proximal direction to a distal direction, and which is openable and closable relative to a treatment section provided in a distal portion of a probe, the gripping unit including: a supporting section in which at least an entire surface thereof is made of an insulating material so as to prevent high-frequency energy from being transmitted through the surface; a swing section which includes a jaw-side facing surface opposed to the treatment section, and a jaw-side electrode section functioning, by being supplied with the high-frequency energy, as an electrode different from a probe-side electrode section which is formed in the treatment section, the swing section being provided swingably about a swing axis relative to the supporting section, the jaw-side facing surface including a jaw-side electrode plane formed by the jaw-side electrode section; and when two directions perpendicular to the extension axis and perpendicular to an open and close directions of the gripping unit are defined as width directions, a coupling member which swingably couples the swing section with the supporting section in such a manner that the supporting section covers the swing section from the distal direction, from both of the width directions, and from the open direction of the gripping unit, and in such a manner that the swing section is externally exposed only on the jaw-side facing surface.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 2 is a cross-sectional view schematically showing a structure of a transducer unit according to the first embodiment;

FIG. 3 is a cross-sectional view schematically showing a structure of a held unit according to the first embodiment;

FIG. 6 is a perspective view schematically showing an exploded structure of the distal portion of the sheath and the jaw, member-by-member, according to the first embodiment;

FIG. 11 is a perspective view schematically showing an exploded structure of the jaw according to the second embodiment, member-by-member;

FIG. 12 is a cross-sectional view, taken in a cross section perpendicular to an extension axis, schematically showing the structure of the jaw according to the second embodiment;

FIG. 15 is a cross-sectional view, taken in a cross section perpendicular to the longitudinal axis, schematically showing a structure of a treatment section and a jaw according to a third modification;

FIG. 16 is a cross-sectional view, taken in a cross section perpendicular to an extension axis, schematically showing a structure of the jaw according to a fourth modification;

FIG. 19 is a cross-sectional view, taken in a cross section perpendicular to an extension axis schematically showing the structure of the jaw according to the fifth modification.

DETAILED DESCRIPTION OF THE INVENTION (First Embodiment)

The first embodiment of the present invention will be explained with reference to FIG. 1 to FIG. 8.

Figure 1:
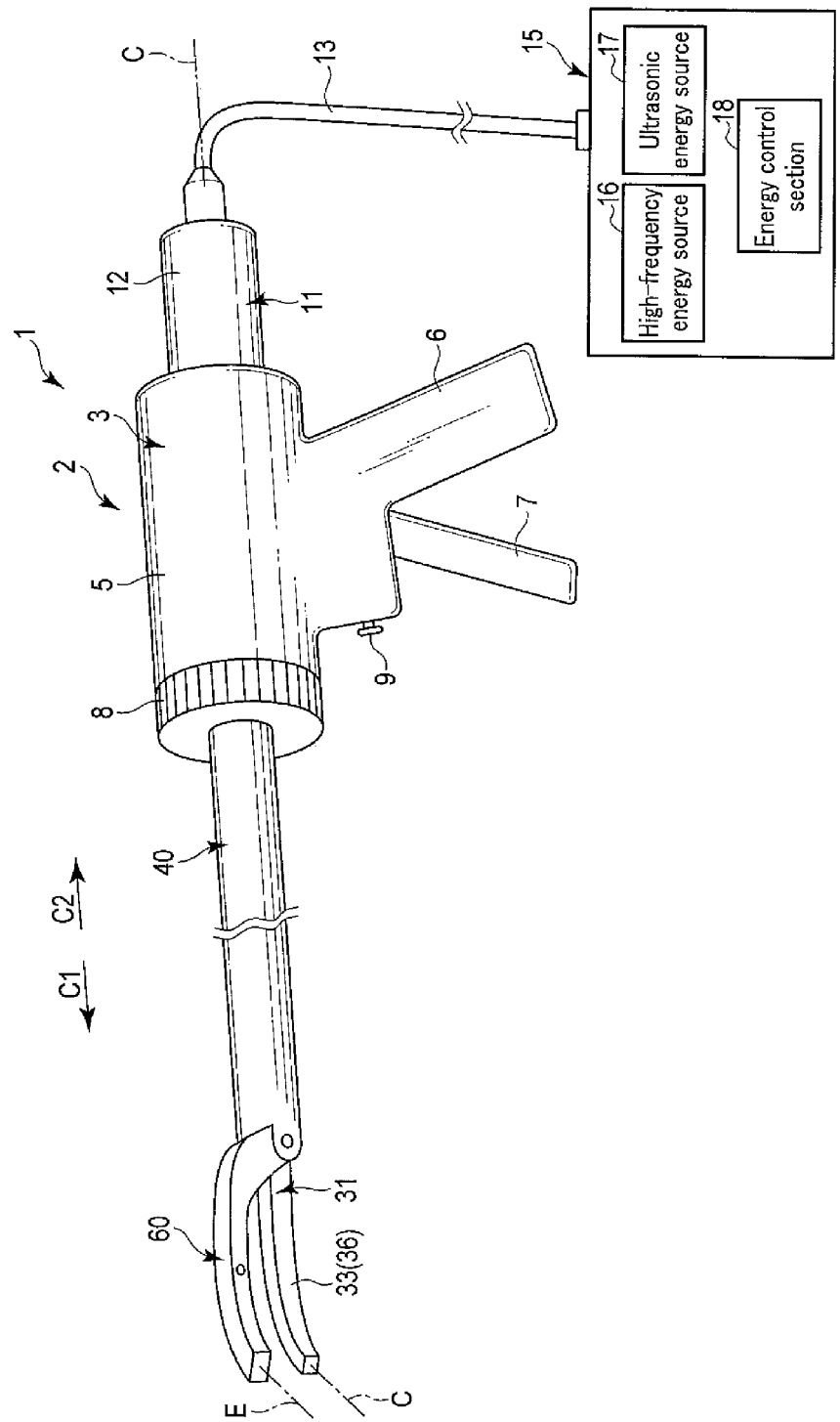
FIG. 1 is a schematic diagram showing a structure of a bipolar treatment apparatus according to a first embodiment.

FIG. 1 shows a bipolar treatment apparatus (a high-frequency treatment apparatus) 1 according to the present embodiment. As shown in FIG. 1, the bipolar treatment apparatus 1 includes a bipolar treatment instrument (a hand piece) 2. The bipolar treatment instrument 2 has a longitudinal axis C. Herein, one of the directions parallel to the longitudinal axis C is defined as a distal direction (indicated by the arrow C1 in FIG. 1), and the other direction opposite to the distal direction is defined as a proximal direction (indicated by the arrow C2 in FIG. 1). The bipolar treatment instrument 2 is an ultrasonic treatment tool configured to perform treatment on a treated target such as living tissue, etc., using an ultrasonic vibration. The bipolar treatment tool 2 is a high-frequency treatment tool which performs treatment using high-frequency energy (a high-frequency current).

The bipolar treatment instrument 2 includes a held unit 3. The held unit 3 includes a cylindrical case 5 extended along the longitudinal axis C, a stationary handle 6 which is integrally formed with the cylindrical case 5, and a movable handle 7 which is rotatably attached to the cylindrical case 5. When the movable handle 7 rotates about a position of attaching to the cylindrical case 5, the movable handle 7 is closed or opened with respect to the stationary handle 6. The held unit 3 includes a rotating operation knob 8 which is attached on the distal direction side of the cylindrical case 5. The rotating operation knob 8 is rotatable about the longitudinal axis C with respect to the cylindrical case 5. An energy operation input button 9 which is an energy operation input section is provided in the stationary handle 6.

The bipolar treatment instrument 2 includes a transducer unit 11. The transducer unit 11 includes a transducer case 12. The oscillator case 12 is integrally rotatable with the rotating operation knob 8 about the longitudinal axis C with respect to the cylindrical case 5. When the transducer case 12 is inserted into an inside of the cylindrical case 5 from the proximal direction side, the transducer case 12 is attached to the held unit 3. One end of a cable 13 is connected to the vibrator case 12. The bipolar treatment apparatus 1 includes a control unit 15. The other end of the cable 13 is connected to the control unit 15. The control unit 15 includes a high-frequency energy source 16, an ultrasonic energy source 17, and an energy control section 18. The high-frequency energy source and the ultrasonic energy source 17 are an electric power generator, for example, and they are composed of an electric power source and a conversion circuit, etc. The energy control section 18 is composed of a processor including a CPU (Central Processing Unit) or an ASIC (Application Specific Integrated Circuit), and a storage section, such as a memory, etc.

FIG. 2 shows a structure of the transducer unit 11. As shown in FIG. 2, the transducer unit 11 includes an ultrasonic transducer 21 which is a vibration generation section provided inside the transducer case 12. The ultrasonic transducer 22 includes a plurality of (four in the present embodiment) piezoelectric elements 22A to 22D configured to convert a current into an ultrasonic vibration. One end of each of electric lines 23A and 23B is connected to the ultrasonic oscillator 21. Each of the electric lines 23A and 23B are extended through the inside of the cable 13, and the other end of each of the electric lines 23A and 23B is connected to the ultrasonic energy source 17 of the control unit 15. The ultrasonic vibration is generated in the ultrasonic transducer 21 by supplying a ultrasonic energy (an ultrasonic current) to the ultrasonic transducer 21 from the ultrasonic energy source 17 via the electric lines 23A and 23B.

The ultrasonic vibrator 21 is attached to a column-shaped horn member 25. The horn member 25 includes a cross-sectional area shift portion in which the area of the cross section perpendicular to the longitudinal axis C changes. The ultrasonic vibration generated in the ultrasonic transducer 21 is transmitted to the horn member 25, and it is transmitted from the proximal direction toward the distal direction in the horn member 25. The amplitude of the ultrasonic vibration transmitted to the horn member 25 is increased in the cross-sectional area taper portion 27. A female thread 28 is provided in a distal portion of the horn member 25.

The bipolar treatment instrument 2 includes a column-shaped probe 31 extended along the longitudinal axis C from the inside of the cylindrical case 7 toward the distal direction. A center axis of the probe 31 is coaxial with the longitudinal axis C. A male thread 32 is provided in a proximal portion of the probe 31. The male thread 32 is screwed into the female thread 28 so as to connect the probe 31 to the horn member 27 on the distal direction side. The probe 31 is connected to the horn member 25 inside the cylindrical case 5. The transducer case 21, the horn member 25, and the probe 31 are integrally rotatable with the rotating operation knob 8 about the longitudinal axis C with respect to the cylindrical case 5.

While the horn member 25 is being connected to the probe 31, the ultrasonic vibration is transmitted from the horn member 25 to the probe 31. The ultrasonic vibration is transmitted along the longitudinal axis C from the proximal direction toward the distal direction in the probe 31. A treatment section 33 is provided in a distal portion of the probe 31. In the probe 31, the ultrasonic vibration is transmitted up to the treatment section 33. The distal end of the probe 31 and the proximal end of the horn member 25 correspond to the anti-node positions of the ultrasonic vibration. Furthermore, the ultrasonic vibration is a longitudinal vibration where a vibration direction and a transmission direction are parallel with the longitudinal axis C.

One end of the electric line 35 is connected to the horn member 25. The electric line 35 is extended through the inside of the cable 13, and the other end of the electric line 35 is connected to the high-frequency energy source 16 of the control unit 15. Thus, a probe-side electricity path of the high-frequency energy (high-frequency electric power) supplied from the high-frequency energy source 16 is formed from the high-frequency energy source 16 through the electric line 36, the horn member 25, and the probe 31 up to the treatment section 33. By transmitting (supplying) the high-frequency energy to the treatment section 33 via the probe-side electricity path, the treatment section 33 functions as an electrode. In other words, the treatment section 33 becomes a probe-side electrode section (a first electrode section) 36 that functions as one of the electrodes of the high-frequency energy (the high-frequency current).

The bipolar treatment instrument 2 includes a sheath 40 extended along the longitudinal axis C. The sheath 40 is attached to the held unit 3 by inserting the sheath 40 into the inside of the rotating operation knob 8 and the inside of the cylindrical case 5. In the inside of the cylindrical case 5, the sheath 40 is attached on the distal direction side of the transducer case 12. The probe 31 is inserted through the sheath 40. The treatment section 33 of the probe 31 is projected from the distal end of the sheath 40 toward the distal direction. A jaw 60 as a gripping unit is rotatably attached in the distal portion of the sheath 40. The jaw (the grip unit) 60 can open and close with respect to the treatment section 33.

FIG. 3 is a diagram showing an inner structure of the held unit 3. As shown in FIG. 3, the sheath 40 includes a connecting cylindrical portion 41 made of an insulating material (a non-conductive material), and a movable cylindrical portion 42 provided on an outer periphery direction side of the connecting cylindrical portion 41. The movable cylindrical portion 42 is made of a conductive material, and movable along the longitudinal axis C relative to the transducer case 12 and the connecting cylindrical portion 41. A slider member 42 made of an insulating material (a non-conductive material) is provided on the outer periphery portion of the movable cylindrical portion 42. The slider member 43 is movable along the longitudinal axis C with respect to the movable cylindrical portion 42. The slider member 42 and the movable cylindrical portion 42 are connected via an elastic member 45, such as a coil spring, etc. The movable handle 7 is attached to the slider member 43. By opening or closing the movable handle 7 relative to the stationary handle 6, a drive force is transmitted to the slider member 43, and the slider member 43 is moved along the longitudinal axis C. Furthermore, the drive force is transmitted from the slider member 43 to the movable cylindrical member 42 via the elastic member 43, and the movable cylindrical portion 42 is moved along the longitudinal axis C with respect to the transducer case 12 and the connecting cylindrical portion 41.

As shown in FIGS. 2 and 3, a case conductive portion is formed in the transducer case 12. One end of the electric line 48 is connected to the case conductive portion 47. The electric line 48 is extended through the inside of the cable 13, and the other end of the electric line 48 is connected to the high-frequency energy source 16 of the control unit 15. A plate-shape contact member 49 made of a conductive material is fixed to the connecting cylindrical portion 41 of the sheath 40. With the sheath 40 being connected to the transducer case 12, the contact member 49 is abutted to the case conductive portion 47 of the transducer case 12, and the movable cylindrical member 42 is movably abutted to the contact member 49. Accordingly, with the sheath 40 being connected to the oscillator case 12, the case conductive portion 47 of the transducer case 12 and the movable cylindrical portion 42 are electrically connected via the contact member 49. Thus, high-frequency energy is supplied (transmitted) to the movable cylindrical portion 42 of the sheath 40 from the high-frequency energy source 12 through the electric line 49 and the case conductive portion 47 of the transducer case 12. The case conductive portion 47 of the transducer case 12 and the movable cylindrical portion 42 of the sheath 40 are electrically insulated from the horn member 25 and the probe 31.

The energy control section 18 controls the output of the ultrasonic energy from the ultrasonic energy source 17 and the output of the high-frequency energy from the high-frequency energy source 16 based on the energy operation input in the energy operation input button 9. A switch (not shown) is provided inside of the stationary handle 6. The switch is closed when the energy operation input button 9 is pressed to input an energy operation. The switch is electrically connected to the energy control section 18. An electric signal is transmitted to the energy control section 18 by closing the switch, and an input of the energy operation is detected. By detecting the input of the energy operation, the ultrasonic energy is output from the ultrasonic energy source 17, and the high-frequency energy is output from the high-frequency energy source 16.

Figure 4:
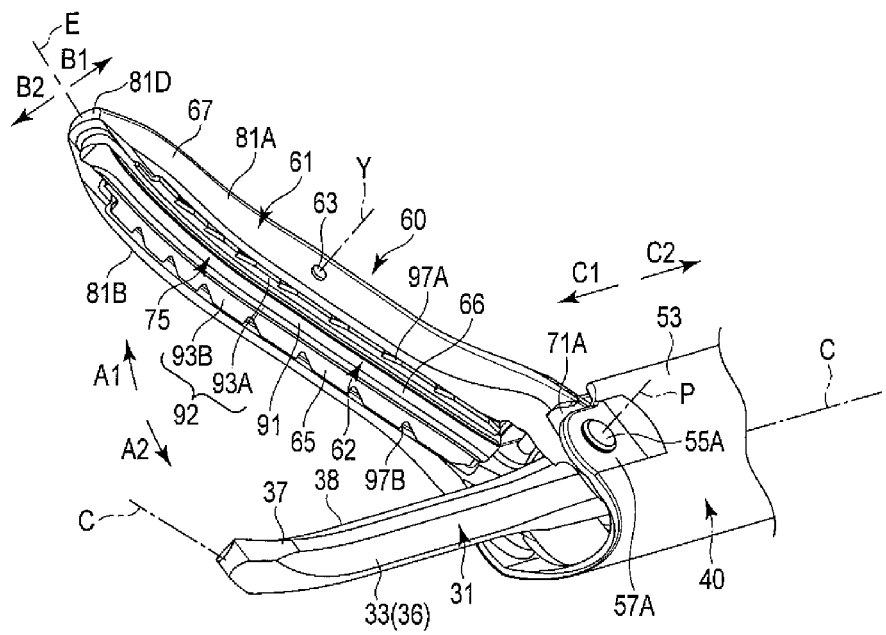
FIG. 4 is a perspective view schematically showing a structure of a distal portion of a sheath, a distal portion of a probe, and a jaw according to the first embodiment.
Figure 5:
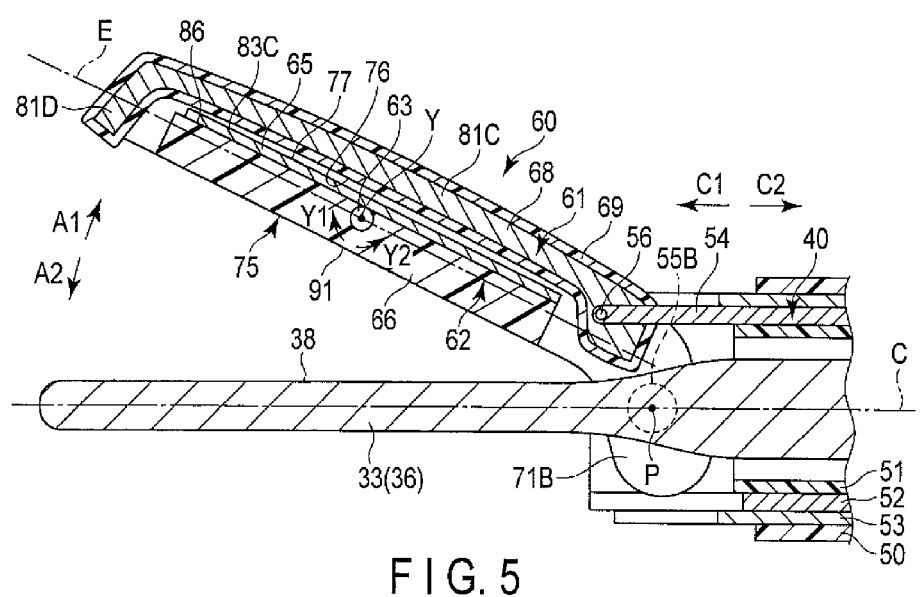
FIG. 5 is a cross-sectional view, taken in a cross section perpendicular to width directions, schematically showing the structure of the distal portion of the sheath, the distal portion of the probe, and the jaw according to the first embodiment.

FIGS. 4 and 5 are diagrams showing the structure of the distal portion of the sheath 40, the distal portion of the probe 31, and the jaw 60, and FIG. 6 is a diagram showing the distal portion of the sheath 40 and the jaw 60. FIGS. 4 and 6 are perspective views, and FIG. 6 is a exploded drawing of the members. As shown in FIG. 4, the jaw serving as a gripping unit is extended along an extension axis (the jaw axis) E from the proximal direction toward the distal direction. The extension axis E is a center axis of the jaw 60, and it is parallel to the longitudinal axis C with the jaw 60 being closed with respect to the treatment section 33. One of the directions perpendicular to the longitudinal axis C and the extension axis E is defined as an open direction of the jaw 60 (the direction indicated by the arrow A1 in FIG. 4), and a direction opposite to the open direction is defined as a close direction of the jaw 60 (the direction indicated by the arrow A2 in FIG. 4). Two directions perpendicular to the extension axis (the longitudinal axis C) and perpendicular to the open and close directions of the jaw are defined as width directions. One of the width directions is referred to as a first width direction (the direction indicated by the arrow B1 in FIG. 4), and the other is referred to as a second width direction (the direction indicated by the arrow B2 in FIG. 4). FIG. 5 is a diagram of a cross section perpendicular to the width directions. FIGS. 4 and 5 show the jaw 60 being opened relative to the treatment section 33.

As shown in FIG. 4, a probe-side curved portion 37 in which the treatment section 33 (the longitudinal axis C) is curved toward the first width direction is formed in the distal portion of the treatment section 33. To provide the probe-side curved portion 37 improves visibility for the operator at the time of performing treatment. A jaw-side curved portion 67 in which the jaw 60 (the extension axis E) is curved toward the first width direction in correspondence with the probe-side curved portion 37 is formed in the jaw 60. By providing the jaw-side curved portion 67, the jaw 60 is extended being opposed to the probe-side curved portion 37.

As shown in FIGS. 5 and 6, the sheath 40 includes an inner tube 51 made of an insulating material (a non-conductive material), a movable pipe 52 provided on the outer periphery direction side of the inner tube 51, an outer pipe 53 provided on the outer periphery direction side of the movable pipe 52, and an outer tube 50 provided on the outer periphery direction side of the outer pipe 53. The movable pipe 52 and the outer pipe 53 are made of a conductive material, and the outer tube 50 is made of an insulating material (a non-conductive material). A proximal portion of the movable pipe 52 is coupled to a distal portion of the movable cylindrical portion 42. When a drive force is transmitted to the movable pipe 52 by the closing motion of the movable handle 7 with respect to the stationary handle 6, the movable pipe 52 is moved integrally with the movable cylindrical portion 42 along the longitudinal axis C relative to the inner tube 51, the outer pipe 53, and the outer tube 50. The movable cylindrical portion 42 and the movable pipe 52 moving along the longitudinal axis C causes the jaw 60 to be closed or open with respect to the treatment section 33. The high-frequency energy transmitted from the high-frequency energy source 16 to the movable cylindrical portion 42 is transmitted to the movable pipe 52 via a fuse pin (not shown). In the present embodiment, the movable cylindrical portion 42 and the movable pipe 52 of the sheath 40 form a high-frequency transmit section (a jaw-side high frequency transmit section). The probe 31 is inserted through the high frequency transmit section (the movable cylindrical section 42 and the movable pipe 52). In other words, the movable cylindrical section 42 and the movable pipe 52 constitute a sheath conductive portion that can transmit a high-frequency current in the sheath 40. The movable pipe 52 which serves as the high frequency transmit section is electrically insulated from the probe 31.

The jaw 60 is attached to the distal portion of the outer pipe 53 of the sheath 40 with pivot pins 55A and 55B being interposed. The jaw 60 rotates about a rotation axis P which is coaxial with the center axis of each of the pivot pins 55A and 55B. The rotation axis P is approximately parallel with the width directions (B1, B2). The distal portion of the movable pipe 52 (the high-frequency transmit section) is connected to the jaw 60 with a connection pin 56 as a connect member being interposed. The high-frequency energy transmitted to the movable pipe 52 is transmitted to the jaw 60 with the connection pin 56. Thus, a jaw-side electric path is formed from the high-frequency energy source 16, through the electric line 48, the case conductive portion 47 of the transducer 12, the movable cylindrical portion 42, and the movable pipe 52, to the jaw 60. The high-frequency energy (high-frequency electric power) is transmitted (supplied) from the high-frequency source 16 to the jaw 60 by the jaw-side electric path.

The jaw 60 serving as the gripping unit includes a supporting section (a jaw main body) 61 attached to the sheath 40, and a swing portion 62 which can swing with respect to the supporting section 61. The swing section 62 is coupled to the supporting section 61 with a couple pin 63 being interposed as a coupling member. The swing section 62 swings about the swing axis Y relative to the supporting section 61. The swing axis Y is parallel with the width directions of the jaw 60, and is coaxial with the center axis of the couple pin 63. In the present embodiment, the swing axis Y passes through a middle portion of the jaw 60 in the direction parallel with the extension axis E. The swing section 62 includes a jaw-side electrode section 65 made of a conductive material, and a pad member 66 attached to the jaw-side electrode section 65. The pad member 66 is made of an insulating material (a non-conductive material). When the high-frequency energy is transmitted (supplied) to the jaw-side electrode section 65 via the above-mentioned jaw-side electric path, the jaw-side electrode section 65 functions as an electrode. In other words, the jaw-side electrode section (second electrode section) 65 functions as the other electrode of the high-frequency energy (a high-frequency current) different from that of the probe-side electrode section (the treatment section 33).

The supporting section 61 includes a supporting main body 68 made of a conductive material, and an insulating coated portion 69 by which an entire surface of the supporting main body 68 is coated. In the supporting section 61, insulation surface finishing is performed on the entire surface, and the entire surface is made of the insulating coated portion 69 (i.e., an insulating material (a non-conductive material)). For this reason, high-frequency energy is not transmitted through the surface of the supporting section 61. It should be noted, however, the high-frequency energy (high-frequency current) can be transmitted in the inside of the supporting section 61, because the supporting main body 68 in the inside of the supporting section 61 is made of a conductive material.

A pair of jaw protruding pieces 71A and 71B is provided in a proximal portion of the support section 61. The jaw protruding piece 71A is located on the first width direction side with respect to the jaw protruding piece 71B, and a space is formed between the jaw protruding pieces 71A and 71B in the width directions. A through-hole 72A which penetrates the jaw protruding piece 71A in the width directions is formed in the jaw protruding piece 71A, and a through-hole 72B which penetrates the jaw protruding piece 71B in the width directions is formed in the jaw protruding piece 71B. A pair of sheath protruding pieces 57A and 57B is provided in the distal portion of the outer pipe 53. A through-hole 58A which penetrates the sheath protruding piece 57A in the width directions is formed in the sheath protruding piece 57A, and a through-hole 58B which penetrates the sheath protruding piece 573 in the width directions is formed in the sheath protruding piece 57B. The sheath protruding piece 57A is abutted to the jaw protruding piece 71A from the first width direction side, and the sheath protruding piece 57B is abutted to the jaw protruding piece 71B from the second width direction side. In a state where the jaw 60 is attached to the sheath 40, the pivot pin 55A is inserted into the through-hole 58A of the sheath protruding piece 57A and the through-hole 72A of the jaw protruding piece 71A from the first width direction side, and the pivot pin 55B is inserted into the through-hole 58B of the sheath protruding piece 57B and the through-hole 72B of the jaw protruding piece 71B from the second width direction side.

A movable projection 54 is formed in the distal portion of the movable pipe 52. The movable projection 54 is located in the space between the jaw protruding pieces 71A and 71B in the width directions. A connection hole 73A which penetrates the jaw protruding piece 71A in the width directions is formed in the jaw protruding piece 71A, and a connection hole 73B which penetrates the jaw protruding piece 71B in the width directions is formed in the jaw protruding piece 71B. A through-hole 59 which penetrates the movable projection 54 in the width directions is formed in the movable projection 54. The connection pin 56 is inserted through the connection hole 73A of the jaw protruding piece 71A, the through-hole 59 of the movable projection 54, and the connection hole 733 of the jaw protruding piece 71B. The connection pin 56 is in contact with the movable pipe 52 in the movable projection 54, and is also in contact with the supporting main body 68, which is in the inside of the supporting section 61, in the jaw protruding pieces 71A and 71B. For this reason, the high-frequency energy is transmitted, by the connection pin 56 which serves as a connecting member, from the movable pipe (the high frequency transmit portion) to the inside of the supporting section 61, without being passed through the surface (the insulating coated portion 68) of the supporting section 61.

Figure 7:
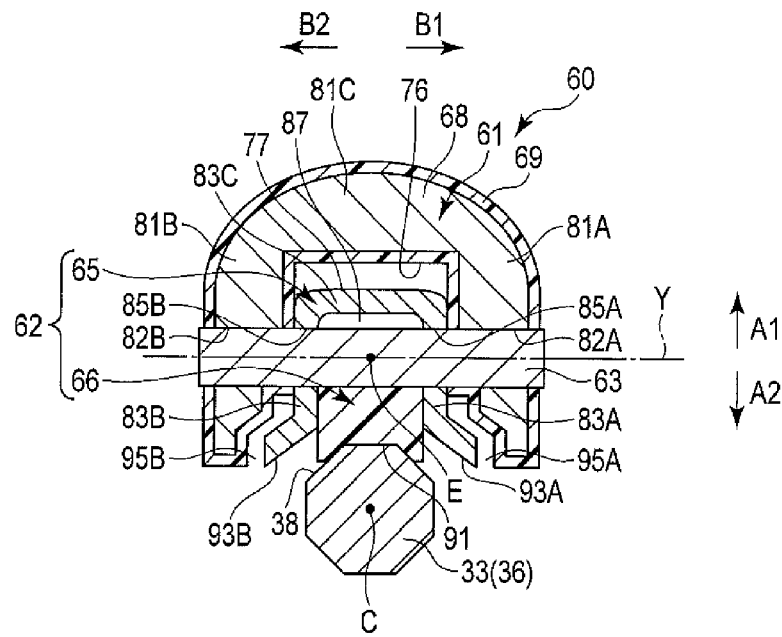
FIG. 7 is a cross-sectional view, taken in a cross section perpendicular to the longitudinal axis, schematically showing a structure of a treatment section and the jaw according to the first embodiment.
Figure 8:
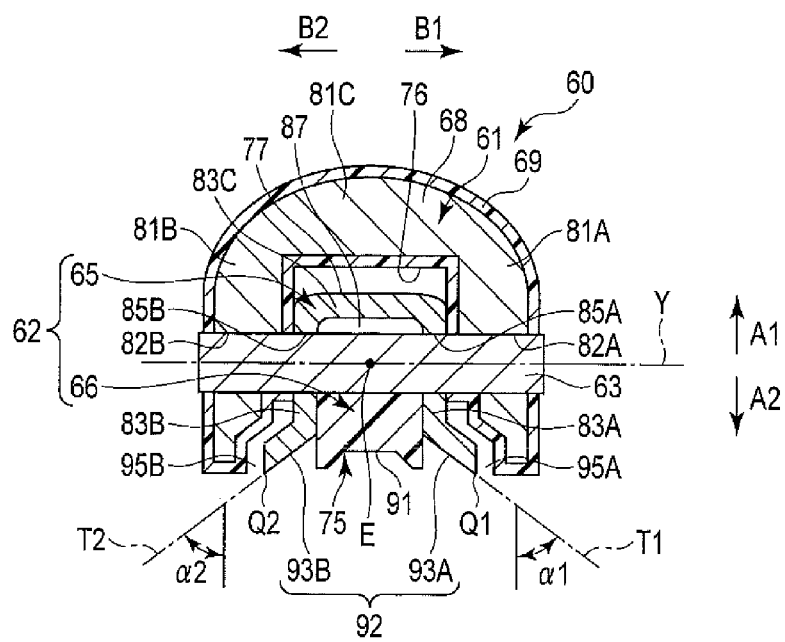
FIG. 8 is a cross-sectional view, taken in a cross section perpendicular to an extension axis, schematically showing the structure of the jaw according to the first embodiment.

FIG. 7 is a diagram showing a cross section of the treatment section 33 and the jaw 60, taken in a cross section perpendicular to the longitudinal axis C (the extension axis E), and FIG. 8 is a diagram showing a cross section of the jaw 60, taken in a cross section perpendicular to the extension axis E. FIGS. 7 and 8 show the cross section passing the swing axis Y of the swing section 62, and FIG. 7 shows the status where the jaw is closed relative to the treatment section 33. As shown in FIGS. 4 to 8, the swing section 62 includes a jaw-side facing surface 75 which faces the treatment section 33 and faces toward the close direction of the jaw 60 (the direction indicated by the arrow A2 in FIGS. 7 and 8). In the present embodiment, the jaw-side electrode section 65 and the pad member 66 constitute the jaw-side facing surface 75. The supporting section 61 covers the swing section 62 from the distal direction, both of the width directions (the first width direction B1 and the second width direction B2), and the open direction of the jaw 60 (the direction indicated by the arrow A1 in FIGS. 7 and 8). The swing section 62 is externally exposed only on the jaw-side facing surface 75. Accordingly, on the surface of the swing section 62, only the jaw-side facing surface 75 is an exposed surface (an outer surface) externally exposed, and the portions other than the jaw-side facing surface 75 are a non-exposed surface (an inner surface) not externally exposed.

The supporting section 61 covers the swing section 62 in such a manner that the space that allows the swing section 62 to swing is formed between the supporting section 61 and the swing section 62. A receiving surface 76 facing toward the close direction of the jaw 60 is provided on the inner surface (the non-exposed surface) of the supporting section 61. An abutting surface 77 facing toward the open direction of the jaw 60 and opposed to the receiving surface 76 is provided on the inner surface of the swing section 62 (the jaw-side electrode section 65). The abutting surface 77 can be abutted to the receiving surface 76. The swing section 62 can swing in a first swing direction (the direction indicated by the arrow Y1 in FIG. 5) and a second swing direction (the direction indicated by the arrow Y2 in FIG. 5). When the swing section 62 swings in the first swing direction, in the swing section 62, a part located on the proximal direction side with respect to the swing axis Y comes closer to the treatment section 33, and a part located on the distal direction side with respect to the swing axis Y comes away from the treatment section 33. Then, when the abutting surface 77 is abutted to the receiving surface 76 at a position located on the distal direction side with respect to the swing axis Y, the swing (movement) of the swing section 62 toward the first swing direction is restricted. On the other hand, when the swing section 62 swings in the second swing direction, in the swing section 62, a part located on the proximal direction side with respect to the swing axis Y comes away from the treatment section 33, and the part located on the distal direction side with respect to the swing axis Y comes closer to the treatment section 33. When the abutting surface 77 is abutted to the receiving surface 77 at a position located on the proximal direction side with respect to the swing axis Y, the swing (movement) of the swing section 62 toward the second swing direction is restricted.

The supporting section 61 includes a first supporting wall 81A covering the swing section 62 from the first width direction side, and a second supporting wall 81B covering the swing section 62 from the second width direction side. The supporting section 61 is further provided with a third supporting wall 81C covering the swing section 62 from the open direction side of the jaw 60, and a fourth supporting wall (a distal supporting wall) 81D covering the swing section 62 from the distal direction side. The receiving surface 76 to which an abutting surface 77 of the swing section 62 can be abutted is formed on the surface (the inner surface) of the third supporting wall 81C. A through-hole 82A, which penetrates the first supporting wall 81A in the width directions, is formed in the first support wall 81A, and a through-hole 82B, which penetrates the second support wall 81B in the width directions, is formed in the second support wall 81B.

The jaw-side electrode section 65 includes a first electrode plate 83A covering the pad member 66 from the first width direction side, and a second electrode plate 835 covering the pad member 66 from the second width direction side. A third electrode plate 83C covering the pad member 66 from the open direction side of the jaw 60 is provided in the jaw-side electrode section 65. An abutting surface 77 which can be abutted to the receiving surface 76 of the supporting section 61 is formed on the surface (the non-exposed surface) of the third electrode plate 83C. A through-hole 85A which penetrates the first electrode plate 83A in the width directions is provided in the first electrode plate 83A, and a through-hole 855 which penetrates the second electrode plate 83B in the width directions is provided in the second electrode plate 83B.

A pad fixed plane 86 which is fixed to the third electrode plate 83C of the jaw-side electrode section 65 is provided on the surface (the inner surface) of the pad member 66. The pad fixed plane 86 faces toward the open direction of the jaw 60, and constitutes an open-direction-side end of the pad (an insulated abutting member) 66. A penetrating groove 87 which penetrates the pad member 66 in the width directions is formed in the pad member 66. The penetrating groove 87 is grooved inward from the pad fixed plane 86 toward the closed direction of the jaw 60.

The couple pin 63 which serves as a coupling member is inserted through the through-hole 82A of the first supporting wall 81A, the through-hole 85A of the first electrode plate 83A, the penetrating groove 87 of the pad member 66, the through-hole 85B of the second electrode plate 83B, and the through-hole 82B of the second supporting wall 81B. The couple pin 63 is in contact with the jaw-side electrode section 65 in the first electrode plate 83A and the second electrode plate 83B, and with the supporting main body 68 provided inside of the supporting section 61 in the first supporting wall 81A and the second supporting wall 81B.

For this reason, the high-frequency energy is transmitted, by the couple pin 63 which serves as a coupling member, from the inside of the supporting section 61 to the jaw-side electrode section 65, without being passed through the surface (the insulating coated portion 68) of the supporting section 61.

A probe-side electrode plane (a probe-side facing surface) 38 facing the jaw-side facing surface 75 is formed in the treatment section 33 which is the probe-side electrode section 36. In the cross section perpendicular to the longitudinal axis C, the treatment section 33 is formed in approximately an octagonal shape. The jaw-side facing surface 75 is provided with an abutting portion (an abutting surface) 91 which can be abutted to the treatment section 33 by closing the jaw 60 relative to the treatment section 33. By closing the jaw 60 with no treated target, such as living tissue, etc. arranged between the jaw 60 and the treatment section 33, the abutting portion 91 is abutted to the probe-side electrode plane 38 of the treatment section 33. In the present embodiment, the abutting portion 91 is formed in the pad member 66, and has electrical insulation properties. Furthermore, the abutting portion 91 is directed in the close direction of the jaw 60.

The jaw-side facing surface 75 includes a jaw-side electrode plane 92 that is formed by the jaw-side electrode section 65. The surface of the jaw-side electrode section 65 is externally exposed only in the jaw-side electrode plane 92. When the abutting portion 91 is abutted to the treatment section 33, the jaw-side electrode plane 92 (the jaw-side electrode section 65) is spaced from the probe-side electrode section 36 (the treatment section 33). Thus, contact between the jaw-side electrode section 65 and the probe-side electrode section 36 can be effectively prevented.

The jaw-side electrode plane 92 includes a first jaw-side electrode plane 93A provided on the first width direction side of the abutting portion 91, and a second jaw-side electrode plane 93B provided on the second width direction side of the abutting portion 91. In the present embodiment, the first jaw-side electrode plane 93A is inclined, in the cross section perpendicular to the extension axis E, for an acute angle of a1 toward the first width direction relative to the close direction of the jaw 60. The second jaw-side electrode plane 93B is inclined, in the cross section perpendicular to the extension axis E, for an acute angle of α2 toward the second width direction relative to the close direction of the jaw 60. In the present embodiment, the first jaw-side electrode plane 93A constitutes a first edge forming plane which forms a first-width-direction-side end Q1 of the jaw-side facing surface 75. The second jaw-side electrode plane 93S constitutes a second edge forming plane which forms a second-width-direction-side end Q2 of the jaw-side facing surface 75.

Herein, a first virtual plane T1 which is an extension of the first jaw-side electrode plane (the first edge forming plane) 93A toward the first width direction side is defined, and a second virtual plane T2 which is an extension of the first jaw-side electrode plane (the second edge forming plane) 93B toward the second width direction side is defined. Tn the present embodiment, the first virtual plane T1 is inclined, in the cross section perpendicular to the extension axis E, for the acute angle of α1 toward the first width direction relative to the close direction of the jaw 60. The second virtual plane T2 is inclined, in the cross section perpendicular to the extension axis E, for an acute angle of α2 toward the second width direction relative to the close direction of the jaw 60. The first supporting wall 81A of the supporting section 61 is provided while not projecting toward the close direction of the jaw 60 with respect to the first virtual plane T1. In other words, the close-direction-side end of the first supporting wall 81A is located on the open direction side with respect to the first virtual plane T1. The second supporting wall 81B of the supporting section 61 is provided so as not to be projected toward the close direction of the jaw 60 with respect to the second virtual plane T2. In other words, the close-direction-side end of the second supporting wall 81B is located on the open direction side with respect to the second virtual plane T2.

A space 95A is formed between the first jaw-side electrode plane 93A and the first supporting wall 81A in the width directions. A space 95B is formed between the second jaw-side electrode plane 93B and the second support wall 81B in the width directions. The dimension of each of the space 95A and 95B is 0.1 mm to 0.2 mm in the width directions.

On the jaw-side facing surface 75, a first uneven portion 97A is provided on the first jaw-side electrode plane 93A, and a second uneven portion 97B is provided on the second jaw-side electrode plane 93B. In the first uneven portion 97A, the edge of the first jaw-side electrode plane 93A (the first-width-direction-side end Q1) is uneven. The direction of the ridges and the direction of the furrows in the first uneven portion 97A are parallel to the first jaw-side electrode plane 93A, and are perpendicular to the extension axis E of the jaw 60. In the second uneven portion 97B, the second-width-direction-side edge of the second jaw-side electrode plane 93B (the second-width-direction-side end Q2) is uneven. The direction of the ridges and the direction of the furrows in the second uneven portion 97B are parallel to the second jaw-side electrode plane 93B, and are perpendicular to the extension axis E of the jaw 60. In the present embodiment, each of the uneven portions 97A and 97B is extended approximately parallel with the extension axis E.

Next, the function and advantageous effects of the bipolar treatment instrument 2 (the bipolar treatment apparatus 1) according to the present embodiment are explained. When a treated target, such as living tissue (a blood vessel), etc. is treated using the bipolar treatment instrument 2, the treatment section 33 and the jaw 60 are inserted inside the body. Then, a treated target is positioned between the jaw 60 and the treatment section 33. Under this circumstance, by closing the movable handle 7, the jaw 60 is closed with respect to the treatment section 33, and the treated target is gripped between the swing section 62 of the jaw 60 and the treatment section 33. At this time, the jaw-side facing surface 75 provided in the swing section 62 is abutted to the treated target. The swing section 62 in which the jaw-side facing surface 75 is provided is swingable about the swing axis Y relative to the supporting section 61. For this reason, even when the distal portion of the jaw-side facing surface 75 (the distal portion of the jaw 60) is abutted to the treated target, the force between the jaw and the treatment section to grip the treated target is approximately the same as the case where the proximal portion of the jaw-side facing surface 75 (the proximal portion of the jaw 60) is abutted to the treated target. In other words, the gripping force between the jaw 60 and the treatment section 33 can be maintained almost the same, even when the position where the jaw-side facing surface 75 is abutted to the treated target in a direction parallel to the extension axis E of the jaw 60 (the distal direction and the proximal direction) is changed.

With the treated target being gripped between the jaw 60 and the treatment section 33, an energy operation is input using the energy operation input button 9. When the input of the energy operation is detected by the energy control section 18, the ultrasonic energy (ultrasonic electric power) is output from the ultrasonic energy source 17, and the high-frequency energy (high-frequency electric power) is output from the high-frequency energy source 16. When the ultrasonic energy (an ultrasonic current) is supplied to the ultrasonic transducer 21, the ultrasonic vibration is generated. The generated ultrasonic vibration is transmitted to the probe 31 via the horn member 25, and it is transmitted from the proximal direction toward the distal direction in the probe 31 along the longitudinal axis C. The treatment section 33 vibrates parallel with the longitudinal axis C when the ultrasonic vibration is transmitted to the treatment section 33. The high-frequency energy is transmitted to the probe-side electrode section 36 (the treatment section 33) through the probe-side electric path and to the jaw-side electrode section 65 of the jaw 60 through the jaw-side electric path. Thus, the probe-side electrode section 36 functions as one of the electrodes for the high-frequency energy, and the jaw-side electrode section 65 functions as the other electrode for the high-frequency energy.

When the ultrasonic vibration is transmitted while gripping the treated target, the treatment section 33 vibrates, and frictional heat is generated between the treatment section 33 and the gripped object. The frictional heat causes the treated target to be cut and to coagulate at the same time. A high-frequency current flows between the probe-side electrode section 36 (the probe-side electrode plane 38) and the jaw-side electrode section 65 (the jaw-side electrode plane 92) via the treated target. Thus, the treated target is denatured, and the coagulable property of the treated target is improved.

In the present embodiment, the swing section 62 is covered with the supporting section 61 from the distal direction, both of the width directions, and the close direction of the jaw, and the surface of the swing section 62 is externally exposed only in the jaw-side facing surface 75. For this reason, in the exposed surface of the jaw 60, the parts respectively directed to the width directions (the first and second width directions), the part directed to the distal direction, and the part facing the open direction of the jaw 60 exclusively consists of the supporting section 61. Accordingly, on the exposed surface of the jaw 60, no space, etc. is formed in the parts respectively facing the width directions (the first and second width directions), the part directed to the distal direction, and the part directed to the open direction of the jaw 60. Thus, when the jaw 60 and the treatment section 33 are moved inside the body, living tissue, etc. other than the treated target can be effectively prevented from getting caught in or clogging the jaw 60. Thus, the mobility of the jaw 60 inside the body can be secured, as well as visibility for the operator, and the treatment performance at the time of treatment can be secured.

The entire surface of the supporting section 61 (the outer surface and the inner surface) is covered by the insulating coating 69. For this reason, the high-frequency energy (a high-frequency current) is not transmitted through the surface of the supporting section 61. Thus, even when the outer surface (the exposed surface) of the supporting section 61 is in contact with living tissue, etc. at a location other than the treated target, a high-frequency current will not be discharged from the exposed surface of the supporting section 61. Moreover, in the swing section 62, only the jaw-side facing surface 75 is externally exposed, and the parts other than the jaw-side facing surface 75 will not be in contact with living tissue. For this reason, discharge of a high-frequency current from the parts other than the jaw-side electrode plane 92 of the jaw-side facing surface 75 can be effectively prevented. Thus, the current intensity of a high-frequency current flowing in the treated target gripped between the swing section 62 of the jaw 60 and the treatment section 33 will be higher, thereby securing the performance of treatment which uses the high-frequency energy.

An insulated surface finishing is performed entirely on the surface (the outer surface and inner surface) of the supporting section 61. Accordingly, the surface finishing becomes more simplified in comparison to the case of partially performing an insulated surface finishing, etc. As a consequence, the jaw 60 can be easily manufactured, and the cost of manufacturing the jaw 60 can be reduced.

In the bipolar treatment instrument 2, the high-frequency energy is transmitted from the movable pipe 52 (the high-frequency transmit section) of the sheath 40 to the supporting main body 68 in the inside of the supporting section 61 through the connection pin 56. The high-frequency energy is further transmitted from the inside of the supporting section 61 to the jaw-side electrode section 65 through the couple pin 63. In other words, the high-frequency energy is transmitted to the jaw-side electrode section 65 without passing through the surface of the supporting section 61. Thus, high-frequency energy can be appropriately transmitted to the jaw-side electrode section 65 even when the entire surface of the supporting section 61 has insulation properties.

The first supporting wall 81A covering the swing section 62 from the first width direction side is not projected toward the close direction of the jaw 60 with respect to the first virtual plane T1, which is the extended first jaw-side electrode plane (the first edge-forming surface) 93A in the first width direction side. The second support wall 81B covering the swing section 62 from the second width direction side is not projected toward the close direction of the jaw 60 with respect to the second virtual plane T2, which is the extended second jaw-side electrode plane (the second edge-forming surface) 93B in the second width direction side. For this reason, when the treated target is positioned between the swing section 62 of the jaw 60 and the treatment section 33, the treated target gets easily caught by the first supporting wall 81A and the second supporting wall 81B of the supporting section 61. Thus, it becomes easy to position the treated target between the swing section 62 of the jaw 60 and the treatment section 33, and the treatment performance during treatment can be improved.

The first uneven portion 97A and the second uneven portion 97B are provided on the jaw-side facing surface 75 of the swing section 62. When the treated target is gripped between the swing section 62 and the treatment section 33, the movement of the treated target along the extension axis E (the longitudinal axis C) is restricted by the first uneven portion 97A and the second uneven portion 973. Thus, the treated target can be securely gripped between the swing section 62 of the jaw 60 and the treatment section 33, and the treatment performance during treatment can be improved.

(Second Embodiment)

The second embodiment of the present invention will be explained with reference to FIG. 9 to FIG. 12. The second embodiment is a transformation of the structure of the first embodiment as will be described below. The elements same in the first embodiment are specified by the same reference numbers, and a duplicate description of such elements will be omitted.

Figure 9:
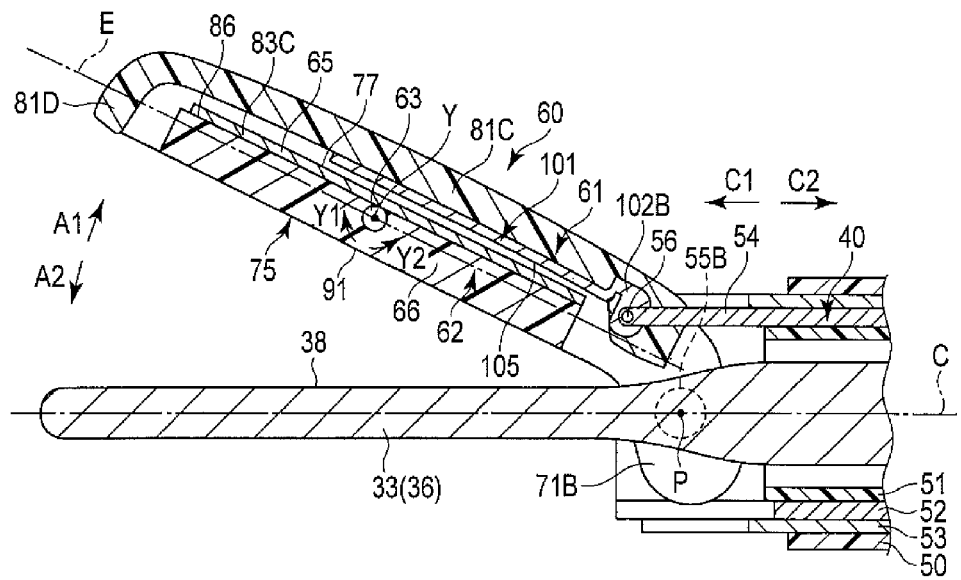
FIG. 9 is a cross-sectional view, taken in a cross section perpendicular to width directions, schematically showing a structure of a distal portion of a sheath, a distal portion of a probe, and a jaw according to a second embodiment.
Figure 10:
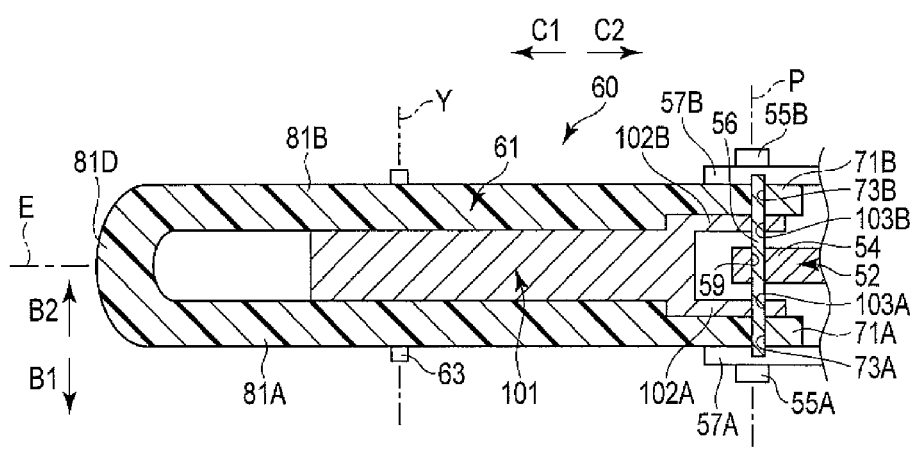
FIG. 10 is a cross-sectional view, taken in a cross section perpendicular to open and close directions, schematically showing the structure of the distal portion of the sheath and the jaw according to the second embodiment.

FIG. 9 shows the structure of the distal portion of the sheath 40, the distal portion of the probe 31, and the jaw 60. FIG. 10 is a drawing showing the structure of the distal portion of the sheath 40 and the jaw 60, and FIGS. 11 and 12 are drawings showing the structure of the jaw 60. FIG. 9 is shown in a cross section perpendicular to the width directions (the directions indicated by the arrows B1 and B2 in FIGS. 10 and 12), and FIG. 10 is shown in a cross section perpendicular to the open and close directions (the directions indicated by the arrows A1 and A2 in FIGS. 9 and 12) of the jaw 60 and passing the connection pin 56. FIG. 11 shows an exploded structure, member-by-member, and FIG. 12 is shown in a cross section perpendicular to the extension axis E and passing the swing axis Y.

As shown in FIGS. 9 to 12, a supporting section 61 and a swing section 62 are provided in the jaw 60 which serves as a gripping unit in the present embodiment, similarly to the first embodiment. It should be noted, however, the entire supporting section 61 is made of an insulating material (a non-conductive material). The entire supporting section 61 is made of a material having low heat conductivity, and the heat conductivity is therefore low in the supporting section 61. The supporting section 61 is made of, for example, a resin material such as PI, PEEK, etc., or a foamed resin, or a ceramic. In the present embodiment, a relay member 101 is provided between the third supporting wall 81C of the supporting section 61 and the third electrode plate 83C of the jaw-side electrode section 65 of the swing section 62 in the open and close directions of the jaw 60. The relay member 101 is made of a conductive material, and is provided without being externally exposed. The relay member 101 is extended approximately parallel with the extension axis E. The relay member 101 is fixed to the third supporting wall 81C of the supporting section 61. Accordingly, the swing section 62 is attached swingably about the swing axis Y with respect to the relay member 101. The relay member 101 is located to be spaced from the abutting surface 77 of the jaw-side electrode section 65, which forms the open-direction-side end of the swing section 62.

A pair of member protruding pieces 102A and 102B is provided in the proximal portion of the relay member 101. A connection hole 103A which penetrates the member protruding piece 102A in the width directions is provided in the member protruding piece 102A, and a connection hole 103B which penetrates the member protruding piece 102B in the width directions is provided in the member protruding piece 102B. The member protruding piece 102A is located between the jaw protruding piece 71A and the movable projection 54 in the width directions, and the member protruding piece 102B is located between the jaw protruding piece 71B and the movable projection 54 in the width directions. In the present embodiment, the connection pin 56 is inserted through the connection hole 73A of the jaw protruding piece 71A, the connection hole 103A of the member protruding piece 102A, the through-hole 59 of the movable projection 54, the connection hole 103B of the member protruding piece 102B, and the connection hole 73B of the jaw protruding piece 71A. The connection pin 56 is in contact with the movable pipe 52 in the movable projection 54, and is also in contact with the relay member 101 in the member protruding piece 102A and the member protruding piece 102B. For this reason, high-frequency energy is transmitted, by the connection pin 56 which serves as a connecting member, from the movable pipe 52 (the high frequency transmit portion) to the relay member 101, without being passed through the supporting section 61 having overall insulation properties.

The distal end of the relay member 101 is located on the distal direction side with respect to the swing axis Y. In other words, the relay member 101 is extended up to a position located on the distal direction side with respect to the swing axis Y. A receiving surface 105 facing the close direction of the jaw 60 is provided in the relay member 101. When the swing section 62 is moved in the first swing direction (the direction indicated by the arrow Y1 in FIG. 9) or in the second swing direction (the direction indicated by the arrow Y2 in FIG. 9), the abutting surface (electric contact surface) 77 of the jaw-side electrode section 65 is in contact with the receiving surface 105 of the relay member 101. When the abutting surface (electric contact surface) 77 of the jaw-side electrode section 65 is in contact with the receiving surface 105 of the relay member 101, the high-frequency energy is transmitted from the relay member 101 to the jaw-side electrode section 65 without being passed through the supporting section 61 having overall insulation properties. Since the distal end of the relay member 101 is located on the distal direction side with respect to the swing axis Y, even in a case where the swing section 62 swings in such a manner that the part located on the distal direction side with respect to the swing axis Y is away from the treatment section 33 (i.e., toward the first swing direction), the abutting surface 77 is in contact with the relay member 101.

In the present embodiment, the swing section 62 is covered with the supporting section 61 from the distal direction, both of the width directions, and the close direction of the jaw, and the surface of the swing section 62 is externally exposed only on the jaw-side facing surface 75. Moreover, the relay member 101 is provided without being externally exposed. Thus, similar to the first embodiment, living tissue, etc. other than the treated target can be effectively prevented from getting caught in or clogging the jaw 60. Furthermore, similar to the first embodiment, since discharge of a high-frequency current from a parts other than the jaw-side electrode plane 92 can be effectively prevented, the current intensity of a high-frequency current flowing in the treated target gripped between the swing section 62 of the jaw 60 and the treatment section 33 becomes higher.

In the present embodiment, since the entire supporting section 61 is made of an insulating material, there is no need for a surface finishing, such as an insulation surface finishing, etc., during the manufacture of the supporting section 61. Thus, the jaw 60 can be more easily manufactured, and the cost of manufacturing the jaw 60 can be reduced. Since the entire supporting section 61 is made of an insulating material having a low heat conductivity, the heat conductivity is therefore low in the supporting section 61. As a consequence, heat generated in the vicinity of the jaw-side facing surface 75 during the treatment does not get easily transmitted to the outer surface (the exposed surface) of the supporting section 61. Thus, even when the supporting section 61 is in contact with living tissue, etc. other than the treated target, damage to the living tissue due to heat can be effectively prevented. Furthermore, heat used for treatment is effectively transmitted only to the treated target, such as living tissue, etc., gripped between the jaw-side facing surface 75 (the pad member 66) and the treatment section 33. For this reason, the performance in treating the treated target is improved.

In the bipolar treatment instrument 2, the high-frequency energy is transmitted from the movable pipe 52 (the high-frequency transmit section) of the sheath 40 to the relay member 101 through the connection pin 56. When the abutting surface (the electric contact surface) 77 of the jaw-side electrode section 65 is in contact with the relay member 101, the high-frequency energy is transmitted from the relay member 101 to the jaw-side electrode section 65. In other words, the high-frequency energy is transmitted to the jaw-side electrode section 65 without passing through the supporting section 61 made of an insulating material. Thus, the high-frequency energy can be appropriately transmitted to the jaw-side electrode section 65 even when the entire the supporting section 61 has insulation properties. Furthermore, the distal end of the relay member 101 is located on the distal direction side with respect to the swing axis Y. For this reason, even in a case where the swing section 62 swings in such a manner that the part located on the distal direction side with respect to the swing axis Y is away from the treatment section 33 (i.e., toward the first swing direction), the abutting surface 77 is in contact with the relay member 101. Thus, the high-frequency energy can be more securely transmitted to the jaw-side electrode section 65.

(Modifications)

Figure 13:
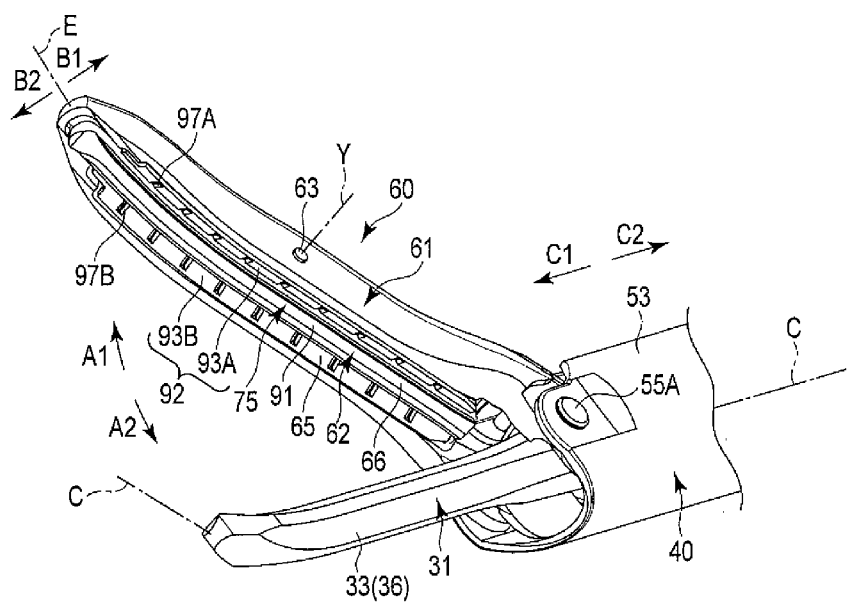
FIG. 13 is a perspective view schematically showing a structure of the distal portion of a sheath, a distal portion of a probe, and a jaw according to a first modification.

In the above-described embodiments, the first uneven portion 97A is provided in the edge of the first jaw-side electrode surface 93A (the first-width-direction-side edge Q1 of the jaw-side facing surface 75), and the second uneven portion 975 is provided in the edge of the second jaw-side electrode plane 93B (the second-width-direction-side edge Q2 of the jaw-side facing surface 75), but is not limited thereto. For example, as shown in FIG. 13 as a first modification, the first uneven portion 97A may be provided on the surface (the exposed surface) of the first jaw-side electrode plane 93A, and the second uneven portion 97B may be provided on the surface (the exposed surface) of the second jaw-side electrode plane 93B. In the present modification, the ridge direction and the furrow direction of the first uneven portion 97A are perpendicular to the first jaw-side electrode plane 93A, and those of the second uneven portion 97B are perpendicular to the second jaw-side electrode plane 935. In the present modification, the first uneven portion 97A and the second uneven portion 97B are extended approximately parallel with the extension axis of the jaw 60. In the present modification, when the treated target is gripped between the swing section 62 and the treatment section 33, the movement of the treated target along the extension axis E (the longitudinal axis C) is restricted by the first uneven portion 97A and the second uneven portion 97B.

Figure 14:
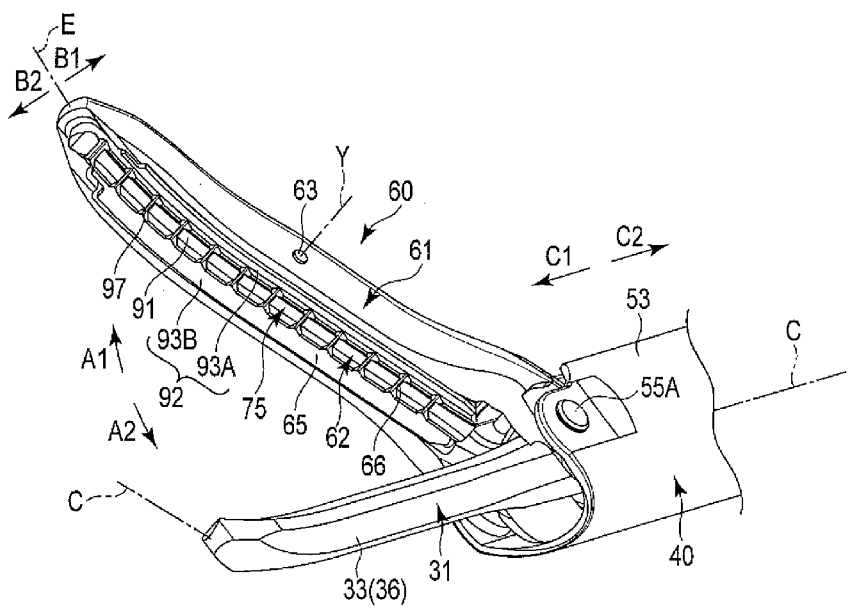
FIG. 14 is a perspective view schematically showing a structure of a distal portion of a sheath, a distal portion of a probe, and a jaw according to a second modification.

As shown in FIG. 14 as a second modification, an uneven portion 97 may be provided on the surface (the exposed surface) of the abutting portion (the abutting surface) 91 of the pad member 66, instead of the first uneven portion 97A and the second uneven portion 97B. In the present modification example, the ridge direction and the furrow direction of the uneven portion 97 are perpendicular to the abutting portion 91. The uneven portion 97 is extended in approximately parallel with the extension axis E of the jaw 60. In the present modification, when the treated target is gripped between the swing section 62 and the treatment section 33, the movement of the treated target along the extension axis E (the longitudinal axis C) is restricted by the uneven portion 97.

As can be seen from the first and second modifications, the uneven portion (97A, 97B; 97) in which the surface or the edge are formed in an uneven shape should be provided on the jaw-side facing surface 75. Thus, the movement of the treated target along the extension axis E (the longitudinal axis C) is restricted when the treated target is gripped between the swing section 62 and the treatment section 33. In the above-described embodiments, etc. the uneven portion (97A, 97B; 97) is extended along the extension axis E; however, the uneven portion is not necessarily extended along the extension axis E. For example, the uneven portion may be extended along the width directions.

In the aforementioned embodiments, an ultrasonic vibration is transmitted to the treatment section 33, but not transmitting the ultrasonic vibration to the treatment section 33 is also acceptable. For example, in the third modification shown in FIG. 15, the pad member 66 is not provided in the swing section 62, and only the jaw-side electrode section 65 forms the swing section 62. In the present modification, no ultrasonic vibration is generated, and the ultrasonic energy source 17, the ultrasonic transducer 21, etc. are not provided.

In the present modification, the receiving portion 107, which is made of an insulating material, is provided in the treatment section 33 in addition to the probe-side electrode section 36. The receiving section 107 is projected from the probe-side electrode section 36 (the probe-side electrode plane 38) toward the open direction (the direction indicated by the arrow A1 in FIG. 15). In the swing section 62, the entire jaw-side facing surface 75 becomes a jaw-side electrode plane 92. In the jaw-side electrode plane 92, a third jaw-side electrode plane 93C is provided in addition to the first jaw-side electrode plane (the first edge forming plane) 93A and the second jaw-side electrode plane (the second edge forming plane) 93B. The third jaw-side electrode plane 93C is extended between the first jaw-side electrode plane 93A and the second jaw-side electrode plane 93B in the width directions, and in the present modification, it is perpendicular with respect to the open and close directions of the jaw 60.

The third jaw-side electrode plane 93C can be abutted to the receiving portion 107 of the treatment section 33 by closing the jaw 60 relative to the treatment section 33. In other words, the third jaw-side electrode plane 93C becomes an abutting portion which is abutted to the receiving portion 107 of the treatment section 33 when the jaw 60 is closed with no treated target, such as living tissue, etc. being arranged between the jaw 60 and the treatment section 33. The jaw-side electrode plane 93C is spaced from the probe-electrode side section 36 (the probe-side electrode plane 38) in a state where the third jaw-side electrode plane 93C which is an abutting portion is abutted to the receiving portion 107. Thus, also in the present modification, the jaw-side electrode section 65 is prevented from being in contact with the probe-side electrode section 36.

As can be seen from the third modification, the abutting portion (91; 93C) that can be abutted to the treatment section 33 is provided on the jaw-side facing surface 75 in the swing section 62 of the jaw 60. When the abutting portion (91; 93C) is abutted to the treatment section 33, the jaw-side electrode section 65 is spaced from the probe-side electrode section 36.

Next, the fourth modification will be described with reference to FIG. 16. As shown in FIG. 16, similar to the first embodiment, in the present modification the swing section 62 is covered with the supporting section 61 from the distal direction, both of the width directions (the directions indicated by the arrows B1 and B2 in FIG. 16), and the open direction of the jaw 60 (the direction indicated by the arrow A1 in FIG. 16), and it is externally exposed only on the jaw-side facing surface 75. In the present modification, a filler 111A is filled in the space 95A between the first jaw-side electrode plane (the first edge forming surface) 93A and the first supporting wall 81A in the width directions. Furthermore, a filler 111B is filled in the space 95B between the second jaw-side electrode plane (the second edge forming surface) 93B and the second supporting wall 818 in the width directions. The filler 111A, 111B has elasticity, and it is, for example, a gel, such as an α gel, etc.

In the present modification, the filler 111A is filled in the space 95A, and the filler 111B is filled in the space 95B. Thus, similar to the first embodiment, living tissue, etc. other than the treated target can be effectively prevented from getting caught in or clogging the space 95A and 95B. The fillers 111A and 111B have elasticity, and even when the filler (111A or 111B) corresponding to each of the space 95A and 95B is filled, the swing section 62 is swingable relative to the support section 61.

In the present modification, the shape of the cross section perpendicular to the extension axis of the supporting section 61 and the swing section 62 (the jaw-side electrode section 65) is different from that in the first embodiment; however, the shape is not limited to that in the first embodiment or in the present modification. In other words, the support sectioning 61 and the swing section 62 should be formed in a shape so that the swing section 62 is covered with the supporting section 61 from distal direction, both of the width directions and the open direction of the jaw 60, and the swing section 62 is exposed to the external only on the jaw-side facing surface 75.

Figure 17:
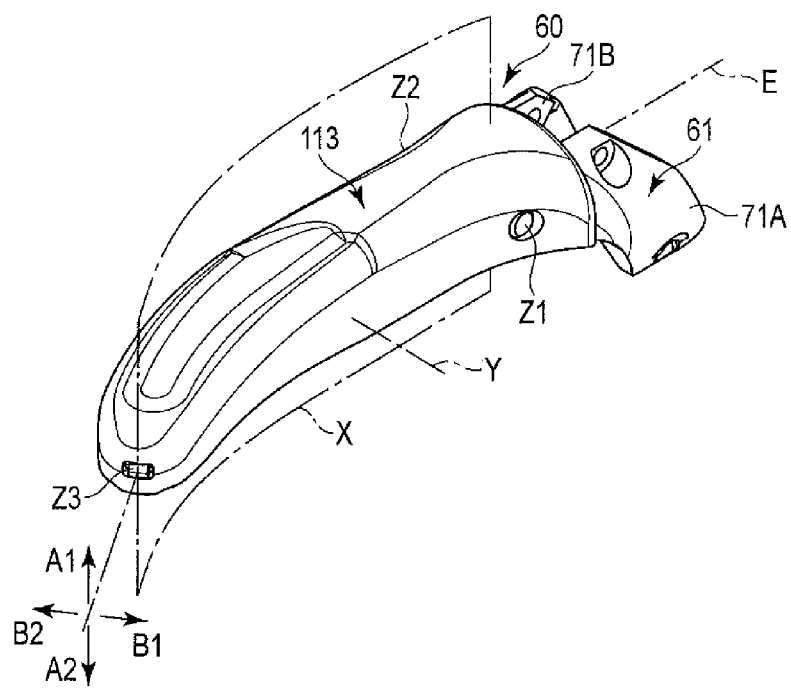
FIG. 17 is a perspective view schematically showing a structure of the jaw according to a fifth modification.
Figure 18:
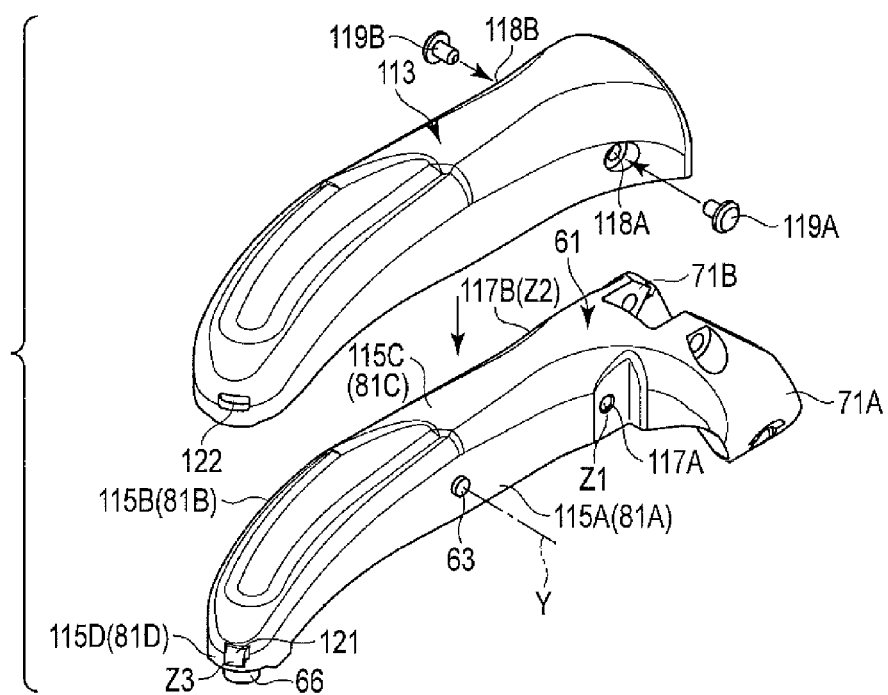
FIG. 18 is a perspective view schematically showing the structure of the jaw according to the fifth modification in a state where a cover member is removed from a supporting section.

The fifth modification will be explained with reference to FIG. 17 to FIG. 19. As shown in FIG. 17 to FIG. 19, a cover member 113 is attached to the supporting section 61 in the present modification. The cover member 114 covers the supporting section 61 from the distal direction, both of the width directions (the first and second width directions), and the open direction of the jaw 60. The cover member 113 is made of a material having insulation properties and heat insulation properties, such as a resin, etc.

Since the entire surface of the supporting section 61 (the outer surface and the inner surface) is covered by the insulating coating 69, a high-frequency current is not discharged from the outer surface of the supporting section 61. However, the inside of the supporting section 61 is made from the supporting main body 68 having high heat conductivity. For this reason, the heat generated in the vicinity of the jaw-side facing surface 75 during the treatment can be easily transmitted to the outer surface of the supporting section 61. Accordingly, in the present modification, the cover member 113 covers the outer surface of the supporting section 61. As a consequence, a contact between the supporting section 61 and living tissue, etc. other than the treated target can be effectively prevented. Furthermore, the cover member 113 is made of a material with heat insulation properties, and has low heat conductivity. Thus, even when the outer surface (the exposed surface) of the cover member 113 is in contact with living tissue, etc. other than the treated target, damage to the living tissue due to heat can be effectively prevented.

The outer surface of the supporting section 61 externally exposed by not being covered with the cover member 113 include a first outer surface 115A facing the first width direction (the direction indicated by the arrow B1 in FIGS. 17 and 19), and a second outer surface 115B directed in the second width direction (the direction indicated by the arrow B2 in FIGS. 17 and 19). The outer surface of the supporting section 61 includes a third outer surface 115C facing to the open direction of the jaw 60 (the direction indicated by the arrow A1 in FIGS. 17 and 19), and the fourth outer surface (the distal outer surface) 115D directed to the distal direction (the direction indicated by the arrow C1 in FIG. 17). The first outer surface 115A is the outer surface of the first supporting wall 81A, and the second outer surface 115B is the outer surface of the second supporting wall 81B. The third outer surface 115C is the outer surface of the third supporting wall 81C, and the fourth outer surface 115D is the outer surface of the fourth supporting wall 81D.

With the cover member 113 attached to the supporting section 61, the supporting section 61 is connected to the cover member 113 at three connection positions, a first connection position Z1, a second connection position Z2, and a third connection position Z3. On the first outer surface 115A of the supporting section 61, the first connection position Z1 is located on the proximal direction side with respect to the swing axis Y. An engaging hole 117A is provided at the first connection position Z1 of the supporting section 61. A through-hole 118A is provided in the cover member 113 so as to correspond to the engaging hole 117A. When the connection pin 119A is inserted through the through-hole 118A and engages with the engaging hole 117A, the supporting section 61 is connected to the cover member 113 at the first connection position Z1. The second connection position Z2 is located on the proximal direction side with respect to the swing axis Y on the second outer surface 115B of the support section 61. An engaging hole 117B is provided at the second connection position Z2 of the supporting section 61. A through-hole 118B is provided in the cover member 113 so as to correspond to the engaging hole 117B. When the connection pin 119B is inserted through the through-hole 118B and engages with the engaging hole 117B, the supporting section 61 is connected to the cover member 113 at the second connection position Z2.

Herein, a jaw center plane X, which is a plane crossing a center position of the jaw 60 in the width directions, is defined. The extension axis E, which serves as the central axis of the jaw 60, is extended on the jaw-center plane X. In the present modification, the third connection position Z3 is located on the fourth outer surface (the distal outer surface) 115D of the supporting section 61, and the jaw center plane X passes the third connection position Z3. Since the third connection position Z3 is located on the fourth outer surface 115D, it is located on the distal direction side with respect to the swing axis Y. An engaging projection 121 which is projected toward the distal direction is provided at the third connection position Z3 of the supporting section 61. An engaging hole 122 is provided in the cover member 113 so as to correspond to the engaging hole 121. When the engaging projection 121 engages with the engaging hole 122, the supporting section 61 is connected to the cover member 113 at the third connection position Z3.

By connecting the supporting section 61 to the cover member 113 at the above-described three connection positions (Z1, Z2, and Z3), the secure and solid attachment of the cover member 113 to the supporting section 61 can be realized with an easy and simple structure.

In the present modification, the third connection position Z3 is located on the fourth outer surface (the distal outer surface) 115D, and the jaw center plane X passes the third connection position Z3, but is not limited thereto. For example, as a modification, the third connection position Z3 may be located on the third outer surface 115C facing the open direction of the jaw 60 as long as the jaw center plane X passes the third connection position Z3 and the third connection position Z3 is located on the distal direction side with respect to the swing axis Y. As another modification, the jaw center plane X does not have to pass the third connection position Z3 as long as the third connection position X3 is located on the fourth outer surface (the distal outer surface) 115D.

As long as the supporting section 61 is connected to the cover member 113 at the above-mentioned three connection positions (Z1, Z2, and Z3), the structure of connecting the supporting section 61 to the cover member 113 is not limited to the structure of the present modification. For example, in a modification, an engaging hole (not shown) is provided at the third connection position Z3 of the supporting section 61, and an engaging projection (not shown) may be provided in the cover member 113 so as to correspond to the engaging hole.

In the present modification, a space 123 is formed between the outer surface of the supporting section 61 and the inner surface of the cover member 113 in parts other than the first to third connection positions Z1 to Z3. The space 123 prevents the cover member 113 being in contact with the supporting section 61 other than the first to third connection positions Z1 to Z3. For this reason, the heat conductivity from the outer surface of the supporting section 61 to the cover member 113 becomes lower. Thus, the heat generated in the vicinity of the jaw-side facing surface 75 during the treatment is much less easily transmitted to the outer surface (the exposed surface) of the cover member 113.

In a modification, a filler (not shown) made of a heat-insulating material may be filled in the space 123 between the supporting section 61 and the cover member 113. The filler is a gel, such as an α gel, etc.

In the above-described embodiments, etc., the swing axis Y of the swing section 62 is parallel with the width directions, but is not limited thereto. For example, in a modification, the swing axis (Y) of the swing section 62 may be provided parallel with the extension axis E.

In the above-described embodiments, etc., the couple pin 63 is used as a coupling member to swingably couple the swing section 62 to the supporting section 61, but is not limited thereto. For example, in a modification, similar to U.S. Patent Application Publication No. 2011/0278343, a spring may be used as a coupling member, and in another modification, a joint ball may be used as a coupling member.

In the above-described embodiments, a gripping unit (the jaw 60) includes a support section (61) in which at least its entire surface is made of an insulating material so as to prevent high-frequency energy from being transmitted through the surface. The gripping unit (60) is provided with a swing section (62) which is swingable about the swing axis (Y) relative to the supporting section (61). The swing section (62) includes a jaw-side facing surface (75) facing the treatment section (33), and a jaw-side electrode section (65) which functions as an electrode different from a probe-side electrode section (36) when the high-frequency energy is transmitted, and the jaw-side facing surface (75) includes a jaw-side electrode plane (92) which is formed by the jaw-side electrode section (65). The swing section (62) is coupled to the support section (61) by a coupling member (63) in a state where the support member (61) covers the swing section (62) from the distal direction (C1), both of the width directions (B1 and B2), and the open direction (A1) of the jaw (60), and the swing section (62) is externally exposed only on the jaw-side facing surface (75).

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A gripping unit which, relative to a probe extended along a longitudinal axis, is extended along an extension axis from a proximal direction toward a distal direction, and which is openably and closably provided perpendicular to the extension axis, the gripping unit comprising:

a supporting section which constitutes a part of the gripping unit, and in which at least an entire surface thereof is made of an insulating material, the supporting section including a receiving surface which is provided on an inner surface not externally exposed and which faces a close direction relative to the probe of the gripping unit, and a supporting wall which is projected from the receiving surface toward the close direction of the gripping unit;

a swing section swingably provided about a swing axis relative to the supporting section, wherein the swing axis is an axis perpendicular to the extension axis and the close direction, the swing section including a jaw-side facing surface opposed to the probe, an abutting surface opposed to the receiving surface, and a side surface extended between the jaw-side facing surface and the abutting surface, the jaw-side facing surface including a jaw-side electrode plane which gives a high-frequency current to a treated target gripped between the jaw-side facing surface and the probe when high-frequency energy is transmitted, and an edge forming plane which forms an end of the jaw-side facing surface in width directions parallel to the swing axis;

a coupling member which swingably couples the swing section with the supporting section and which, when the receiving surface is in parallel with the extension axis, locates a projection end on an open direction side relative to the probe of the gripping unit with respect to a virtual plane which is an extension of the edge forming plane toward an outer side in the width directions, wherein the projection edge is a distal end of a part projected in the supporting wall from the receiving surface toward the close direction with respect to the side surface; and a cover member which is made of a material having insulation properties and heat insulation properties, which is extended in a part located on a distal direction side with respect to the supporting section, a part located on both sides of the width directions with respect to the supporting section, and a part located on an opening direction side of the gripping unit with respect to the supporting section, and which is attached to the supporting section.

2. The gripping unit according to claim 1, wherein the cover member is connected to the supporting section at a first connection position, a second connection position, and a third connection position when the cover member is attached to the supporting section, the supporting section includes a first outer surface facing a first width direction which is one of the width directions, and a second outer surface facing a second width direction opposite to the first width direction, the first connection position is located on a proximal direction side with respect to the swing axis on the first outer surface, the second connection position is located on the proximal direction side with respect to the swing axis on the second outer surface, the third connection position is located on the distal direction side with respect to the swing axis, and when a jaw-center plane which crosses a center position of the gripping unit in the width directions is defined, the jaw center plane passes the third connection position.

3. The gripping unit according to claim 1, wherein
the cover member is connected to the supporting section at a first connection position, a second connection position, and a third connection position when the cover member is attached to the supporting section,
the supporting section includes a first outer surface facing a first width direction which is one of the width directions, a second outer surface facing toward the second width direction, and a distal outer surface facing toward the distal direction,
the first connection position is located on a proximal direction side with respect to the swing axis on the first outer surface,
the second connection position is located on the proximal direction side with respect to the swing axis on the second outer surface, and
the third connection position is located on the distal outer surface.

4. The gripping unit according to claim 1, wherein
the cover member is connected to the supporting section at a first connection position, a second connection position, and a third connection position when the cover member is attached to the supporting section, and
the cover member is attached to the supporting section without being in contact with any parts except for the first connection position, the second connection position, and the third connection position.

5. A gripping unit which, relative to a probe extended along a longitudinal axis, is extended along an extension axis from a proximal direction toward a distal direction, and which is openably and closably provided perpendicular to the extension axis, the gripping unit comprising:
a supporting section which constitutes a part of the gripping unit, and in which at least an entire surface thereof is made of an insulating material, the supporting section including a receiving surface which is provided on an inner surface not externally exposed and which faces a close direction relative to the probe of the gripping unit, and a supporting wall which is projected from the receiving surface toward the close direction of the gripping unit;
a swing section swingably provided about a swing axis relative to the supporting section, wherein the swing axis is an axis perpendicular to the extension axis and the close direction, the swing section including a jaw-side facing surface opposed to the probe, an abutting surface opposed to the receiving surface, and a side surface extended between the jaw-side facing surface and the abutting surface, the jaw-side facing surface including a jaw-side electrode plane which gives a high-frequency current to a treated target gripped between the jaw-side facing surface and the probe when high-frequency energy is transmitted, and an edge forming plane which forms an end of the jaw-side facing surface in width directions parallel to the swing axis; and
a coupling member which swingably couples the swing section with the supporting section and which, when the receiving surface is in parallel with the extension axis, locates a projection end on an open direction side relative to the probe of the gripping unit with respect to a virtual plane which is an extension of the edge forming plane toward an outer side in the width directions, wherein the projection edge is a distal end of a part projected in the supporting wall from the receiving surface toward the close direction with respect to the side surface,
the supporting wall includes a first supporting wall projected from the receiving surface with respect to the side surface on a first width direction side which is one of the width directions, and second supporting wall projected from the receiving surface with respect to the side surface on a second width direction side which is opposite to the first width direction,
the edge forming plane includes a first edge forming plane which forms a first-width-direction-side end of the jaw-side facing surface, and a second edge forming plane which forms a second-width-direction-side end of the jaw-side facing surface, and
the coupling member locates a projection edge of the first supporting wall on the open direction side of the gripping unit with respect to a first virtual plane which is an extension of the first edge forming plane toward the first width direction, and locates a projection edge of the second virtual plane, which is an extension of the second edge forming plane toward the second width direction side.

6. A jaw for a bipolar treatment instrument having a sheath and a probe, the sheath having a proximal end and a distal end, the probe being inserted through the sheath, a distal portion of the probe protruding from the distal end of the sheath, the jaw being rotatably attached to the distal end of the sheath, the jaw being configured to rotate relative to the sheath so that the jaw can rotate between open and closed positions relative to the distal portion of the probe, the jaw comprising:
a jaw main body rotatably attached to the sheath around a rotation axis and having an exterior surface, the entire exterior surface of the jaw main body having electrical insulation properties, the exterior surface of the jaw main body including a receiving surface facing the distal portion of the probe, the jaw main body including a side wall which extends below the receiving surface towards the distal portion of the probe;
a swing section which is configured to rotate integrally with the jaw main body relative to the sheath and which is swingably attached to the jaw main body around a swing axis, the swing axis being parallel to the rotation axis, the swing section including a top surface opposed to the receiving surface of the jaw main body and a side surface extending from the top surface by a predetermined height, the top surface having electrical conductive properties and being configured to flow high-frequency current between the distal portion of the probe and the top surface of the swing section when high-frequency electric power is supplied to the top surface of the swing section and the distal portion of the probe, the side wall of the jaw main body extending the predetermined height of the side surface.

7. The jaw according to claim 6,
further comprising a coupling member which swingably couples the swing section to the jaw main body,
wherein an inside of the jaw main body is made of a conductive material, and
the high-frequency power is transmitted from the inside of the jaw main body to the top surface of the swing section- via the coupling member.

8. A bipolar treatment instrument comprising:
the jaw according to claim 6, wherein an inside of the jaw main body is made of a conductive material;
a probe having a digital portion and a treatment section in the distal portion, wherein the jaw is openable and closeable relative to the treatment section;

a high-frequency transmit section through which the probe is inserted such that the treatment section extends from the high-frequency transmit section, the high-frequency transmit section is made of a conductive material; and a connecting member which connects the high-frequency transmit section with the jaw main body, and which is configured to transmit the high-frequency power from the high-frequency transmit section to the inside of the jaw main body.

9. The jaw according to claim 6, wherein the entire jaw main body is made of an insulating material, the jaw further comprises a relay member which is made of a conductive material, and which is provided between the jaw main body and the swing section in the open and close directions of the jaw without being externally exposed, the swing section being swingably attached to the relay member about the swing axis, and the top surface of the swing section includes an electric contacting surface to which the high-frequency power is transmitted from the relay member when the electric contacting surface is in contact with the relay member.

10. A bipolar treatment instrument comprising:

the jaw according to claim 9;

a probe which includes a treatment section in the distal portion, wherein the jaw is openable and closeable relative to the treatment section;

a high-frequency transmit section through which the probe is inserted and which is made of a conductive material; and a connecting member which connects the high-frequency transmit section with the relay member, and which is configured to transmit the high-frequency power from the high-frequency transmit section to the relay member.

11. The jaw according to claim 6, wherein the swing section includes a bottom surface facing the probe that includes an uneven portion in which a surface or an edge of the bottom surface is formed in an uneven shape.

12. A bipolar treatment instrument comprising:

the jaw according to claim 6; wherein:

the probe includes a treatment section in the distal portion, wherein the jaw is openable and closeable relative to the treatment section;

the swing section includes a bottom surface facing the probe, the bottom surface includes an electrode plane and an abutting portion abuttable to the treatment section by closing the jaw relative to the treatment section, the treatment section includes a probe-side electrode plane opposed to the bottom surface, and the electrode plane of the bottom surface is spaced from the probe-side electrode plane when the abutting portion is abutted to the treatment section.

13. The bipolar treatment instrument according to claim 12, wherein the probe has a proximal portion and the probe is configured to transmit an ultrasonic vibration from the proximal portion toward the distal portion up to the treatment section, and the abutting portion is made of an insulating material.

14. The bipolar treatment instrument according to claim 12, wherein the treatment section includes a receiving portion which is made of an insulating material, and to which the abutting portion is abuttable.

15. The jaw according to claim 6, wherein the receiving surface has spaced first and second side edges, and the jaw main body includes a first side wall extending from the first side edge and a second supporting side wall extending from the second side edge.

16. A bipolar treatment instrument comprising:

the jaw according to claim 6, wherein:

the probe includes a treatment section in its distal portion, wherein the jaw is openable and closeable relative to the treatment section;

the swing section includes a bottom surface facing the probe; and the treatment section includes a probe-side electrode plane opposed to the bottom surface.

* * * * *